United States Patent
Reed

(10) Patent No.: US 11,066,482 B2
(45) Date of Patent: Jul. 20, 2021

(54) SPECIFIC PLASMIN INACTIVATION BY ANTICATALYTIC ANTIBODY

(71) Applicant: Guy L. Reed, Paradise Valley, AZ (US)

(72) Inventor: Guy L. Reed, Paradise Valley, AZ (US)

( * ) Notice: Subject to any disclaimer, the term of this patent is extended or adjusted under 35 U.S.C. 154(b) by 209 days.

(21) Appl. No.: 16/137,665

(22) Filed: Sep. 21, 2018

(65) Prior Publication Data

US 2019/0085097 A1 Mar. 21, 2019

Related U.S. Application Data

(60) Provisional application No. 62/561,332, filed on Sep. 21, 2017.

(51) Int. Cl.
*C07K 16/40* (2006.01)
*A61P 7/04* (2006.01)
*A61K 39/00* (2006.01)

(52) U.S. Cl.
CPC .......... *C07K 16/40* (2013.01); *A61P 7/04* (2018.01); *A61K 2039/505* (2013.01); *C07K 2317/33* (2013.01); *C07K 2317/52* (2013.01); *C07K 2317/55* (2013.01); *C07K 2317/76* (2013.01); *C07K 2317/92* (2013.01)

(58) Field of Classification Search
None
See application file for complete search history.

(56) References Cited

U.S. PATENT DOCUMENTS

2004/0235115 A1 11/2004 Reed

FOREIGN PATENT DOCUMENTS

WO 2014/116706 A1 7/2014
WO 2015/007727 A1 1/2015

OTHER PUBLICATIONS

Janeway et al., Immunobiology, 3rd edition, 1997 Garland Publishing Inc., pp. 3:1-3:11.*
Rudikoff et al., Proc Natl Acad Sci USA. Mar. 1982. 79(6):1979-83.*
Edwards et al., J Mol Biol. Nov. 14, 2003;334(1):103-18.*
Lloyd et al., Protein Eng Des Sei. Mar. 2009;22(3):159-68. doi: 10.1093/protein/gzn058. Epub Oct. 29, 2008.*
Goel et al., J Immunol. Dec. 15, 2004;173(12)7358-67.*
Kanyavuzetal., Nat Rev Immunol. Jun. 2019;19(6):355-368. doi: 10.1038/S41577-019-0126-7.*

European Search Report and Written Opinion for EP Application No. 18195872.9 dated Dec. 10, 2018 (12 pages).
Ho-Tin-Noe et al., "Functional Hierarchy of Plasminogen Kringles 1 and 4 in Fibrinolysis and Plasmin-Induced Cell Detachment and Apoptosis," FEBS Journal, 2005, 272:3387-3400.
Law et al., "X-Ray Crystal Structure of Plasmin with Tranexamic Acid-Derived Active Site Inhibitors," Blood Advances, 2017, 1(12):766-771.
Smith, "New Horizons in Therapeutic Antibody Discovery: Opportunities and Challenges Versus Small-Molecule Therapeutics," Journal of Biomolecular Screening, 2015, 20(4);437-453.
European Office Action for EP Application No. 18195872.9 dated Mar. 3, 2021 (17 pages).
Berden et al., "Anti-Plasminogen Antibodies Compromise Fibrinolysis and Associate with Renal Histology in ANCA-Associated Vasculitis," J. am. Soc. Nephrol., 2010, 21:2169-2179.
Bu et al., "IgG Antibodies to Plasminogen and Their Relationship to IgG anti-β2-Glycoprotein 1 Antibodies and Thrombosis," Clin Rheumatol., 2008, 27:171-178.
Church et al., "Inhibition of Plasminogen Activation by Monoclonal Antibodies to the Kringle 5-B Chain Segment of Human Plasminogen," Hybridoma, 1991, 10(6):659-672.
Church et al., "A Kringle-Specific Monoclonal Antibody," Hybridoma, 1994, 13(5):423-429.
Greenspan et al., "Defining Epitopes: Its Not as Easy as it Seems," Nature Biotechnology, 1999, 17:936-937.
Lafferty et al., "Immunochemistry of Human Lp[a]: Characterization of Monoclonal Antibodies that Cross-React Strongly with Plasmniogen," Journal of Lipid Research, 1991, 32:277-292.
Nishiya et al., "Determination of a Factor VIII-Interactive Region within Plasmin Responsible for Plasmin-Catalysed Activation and Inactivation of Factor VIII(a)", Thrombosis and Haemostasis, 104:105-117.
XP055032927, Okada et al., 2011; Abstract P-TH-257, "Thursday, Jul. 28, 2011 ", Journal of Thrombosis and Haemostasis, vol. 9, Jul. 1, 2011 (Jul. 1, 2011), pp. 712-959, XP055032927, ISSN: 1538-7933, DOI: 10.1111/1.1538-7836.2011.04380_4.x.
XP004920129, Ueshima et al., "Effect of Mutagenized NH2-Terminal Amino Acid Region on Plasminogen Activator Activity of Staphylokinase," Oral Communications, 1996, p. 8.
Yang et al., "Identification of Anti-Plasmin Antibodies in the Antiphospholipid Syndrome that Inhibit Degradation of Fibrin," The American Association of Immunologists, Inc., 2004, pp. 5765-5773.

* cited by examiner

*Primary Examiner* — Michael Szperka
(74) *Attorney, Agent, or Firm* — Eversheds Sutherland (US) LLP

(57) ABSTRACT

Methods and pharmaceutical compositions for treating hemorrhage or bleeding are provided. The pharmaceutical compositions include an effective amount of an antifibrinolytic composition that reduces or inhibits hemorrhage or bleeding in a subject.

19 Claims, 7 Drawing Sheets
Specification includes a Sequence Listing.

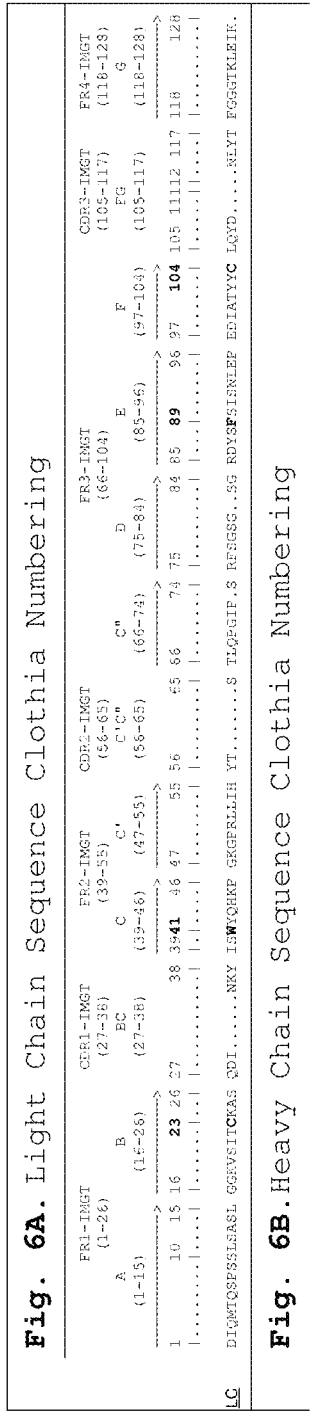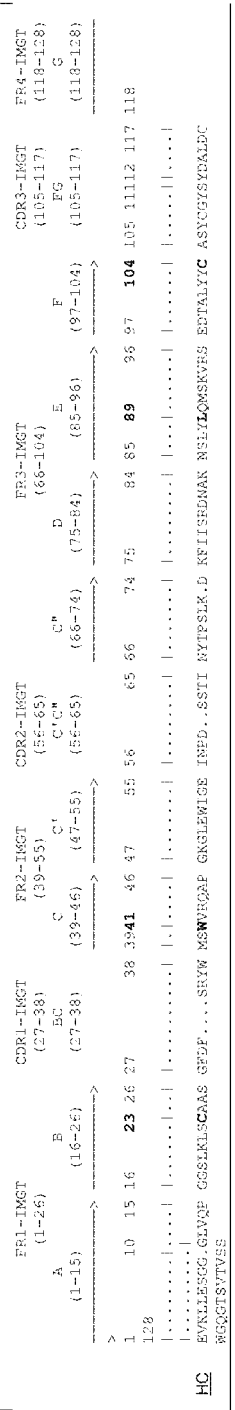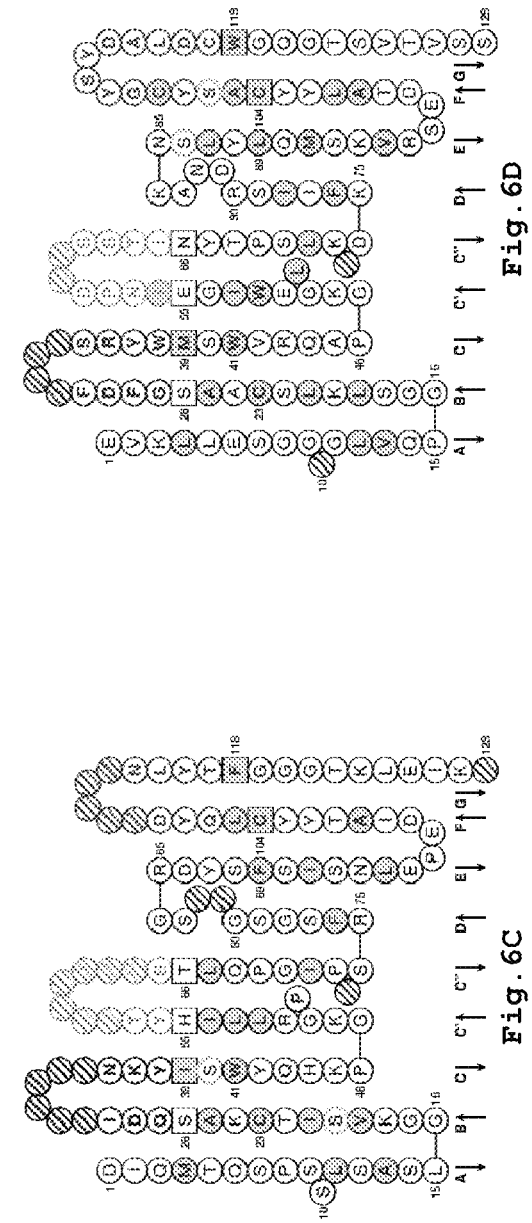
Fig. 6A. Light Chain Sequence Clothia Numbering
Fig. 6B. Heavy Chain Sequence Clothia Numbering
Fig. 6C
Fig. 6D

SPECIFIC PLASMIN INACTIVATION BY ANTICATALYTIC ANTIBODY

CROSS REFERENCE TO RELATED APPLICATIONS

This application claims priority to U.S. Provisional Application No. 62/561,332, filed Sep. 21, 2017, the entire contents of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Sep. 13, 2018, is named 27849-0023_SL.txt and is 27,141 bytes in size.

INTRODUCTION

Hemorrhage, or bleeding, is a serious or fatal complication of surgery, injury or coagulation factor deficiency. Antifibrinolytic agents that inhibit plasmin-mediated fibrinolysis or clot dissolution may reduce blood loss, emergency reoperation, morbidity and death in severe hemorrhage.[1-11] Plasmin activity is regulated by plasmin generation, plasmin substrate interactions and specific inhibitors. Plasmin generation is catalyzed by tissue plasminogen activator (tPA) and urinary-type plasminogen activator (uPA). Plasmin activity is governed by binding interactions with lysine residues on fibrin mediated by plasmin kringles, as well as alterations to fibrin induced by activated factor XIII and by thrombin-activatable fibrinolysis inhibitor. Plasmin activity is also tightly controlled by inhibitors, particularly the fast-acting serpin, α2-antiplasmin and, the less potent inhibitor α2-macroglobulin.[12-15] Unchecked plasmin dissolves thrombi (fibrinolysis) and degrades clotting factors (fibrinogen, factor V, factor VIII), which impairs coagulation, thereby enhancing bleeding risk. In addition, unchecked plasmin activates neutrophils and macrophages, increasing chemotaxis and oxidative stress, as well as promoting release of pro-inflammatory cytokines and matrix metalloproteinases.[16]

Since their first use more than 50 years ago, small molecule plasmin inhibitors have been shown to reduce bleeding and complications. Current plasmin inhibitors are small molecules that block the enzyme active site or interfere with the interactions of plasmin with substrates. There are two classes of current agents, lysine analogs and active site inhibitors.

The lysine analogs, epsilon amino caproic acid (EACA) and tranexamic acid, simulate lysine residues and interact with lysine binding sites on plasmin kringles to block its interactions with fibrin. Due to their molecular size and mechanism of action, the lysine analogs have low potency and modest specificity; they accumulate in kidney disease and penetrate the blood brain barrier and placenta.[2,10-12] The lysine analogs prevent plasminogen and tPA from binding to fibrin, thereby inhibiting plasminogen activation and fibrinolysis. Through the same mechanisms, the lysine analogs may actually increase plasmin activity by blocking kringle interactions with α2-antiplasmin[20] and by enhancing plasminogen activation by tPA or uPA in solution.[21,22] The lysine analogs also interfere with the interactions of plasminogen-plasmin with cellular receptors and block interactions of plasminogen with tissue factor.[23] The biological effects of the interactions of the lysine analogs with other kringle-containing proteins (tPA[24], (pro)thrombin,[25] hepatocyte growth factors, uPA, apoprotein (a) of lipoprotein(a)[25]), are not well understood. Lysine analogs cross the placenta and the blood brain barrier, cause seizures in cardiac surgical patients[26-30] and increase brain infarction in subarachnoid hemorrhage patients. Tranexamic acid is excreted via the urine (95%) unchanged; therefore toxicity risk is significant in patients with kidney disease.[31]

Bovine pancreatic trypsin inhibitor (BPTI, aprotinin) is an active site inhibitor of plasmin. BPTI is more potent than the lysine analogs for stopping cardiac surgical bleeding $_{29,32}$ and for preventing generation of plasmin activity as measured by formation of plasmin-α2-antiplasmin complexes.[33] However, as its name implies, BPTI is also non-specific inhibitor of numerous other serine proteases including trypsin, thrombin, activated protein C (a natural anticoagulant), kallikrein (which activates the kinin system), neutrophil elastase and other proteases.[72] Through these actions, BPTI has broad anticoagulant, antifibrinolytic, anti-inflammatory and other effects.[73] BPTI also accumulates in renal failure and crosses the blood brain barrier.[17] While BPTI is more effective than the lysine analogs at stopping cardiac surgical bleeding, BPTI is no longer available in the U.S. due to safety concerns associated with increased mortality; BPTI is associated with a significant increase in all-cause 30 day mortality.[32]

Clinical studies suggests that fibrinolysis affects bleeding in the millions of patients who undergo cardiac surgery, orthopedic surgery, liver transplantation, vascular surgery, thoracic surgery, gynecological surgery, end-stage renal disease, peripartum bleeding, gastrointestinal bleeding, neurosurgery, trauma, traumatic brain injury, intracerebral bleeding and subarachnoid hemorrhage.[5-11,34-63] Inhibiting fibrinolysis may significantly reduce bleeding related to surgery, trauma or coagulation factor deficiencies. Current fibrinolytic inhibitors are small molecules (epsilon amino caproic acid, EACA and tranexamic acid) or active site inhibitors, which are limited by non-specific mechanisms of action, off-target effects, low potency and lack of efficacy for certain types of hemorrhage. There is a need for fibrinolytic inhibitors with greater specificity and potency, particularly in patients with serious, life-threatening hemorrhage, such as brain bleeding where current therapies are ineffective and may be harmful, in part because of off-target effects. The surface loops surrounding the active site of plasmin are unique and are known to mediate highly specific interactions of plasmin with substrates and other molecules.[18] Creating highly specific catalytic inhibitors of plasmin is challenging, because its enzymatic active site has significant homology with other trypsin-like serine proteases. Reflecting this challenge, the most potent and specific inhibitor of plasmin, α2-antiplasmin, also rapidly inhibits trypsin and interacts with other serine proteases.

SUMMARY OF THE INVENTION

This disclosure provides antibodies and other binding molecules directed against unique loop structures in the plasmin protease domain, and the antibodies act as a highly specific inhibitor of plasmin-mediated fibrinolysis in vitro and surgical bleeding in vivo.

In embodiments, the invention provides a method of inhibiting plasmin activity in a subject in need thereof comprising administering to the subject an effective amount of a plasmin inhibiting composition comprising a plasmin protease domain-specific monoclonal antibody or functional fragment thereof.

In embodiments, the invention provides a method of inhibiting plasmin-mediated fibrinolysis in a subject in need thereof comprising administering to the subject an effective amount of a plasmin inhibiting composition comprising a plasmin protease domain-specific monoclonal antibody or functional fragment thereof.

In embodiments, the invention provides a method of treating hemorrhage in a subject in need thereof comprising administering to the patient an effective amount of a pharmaceutical composition comprising a plasmin protease domain-specific monoclonal antibody or functional fragment thereof and a pharmaceutically acceptable excipient.

In embodiments, the invention provides that the monoclonal antibody or functional fragment thereof inhibits fibrinolysis. In embodiments, the invention provides that the monoclonal antibody or functional fragment thereof inhibits plasmin cleavage of Factor V protein. In embodiments, the invention provides that the monoclonal antibody or functional fragment thereof inhibits plasmin cleavage of tripeptide paranitroanilide substrate more potently than epsilon amino caproic acid.

In embodiments, the invention provides the subject is a human.

In embodiments, the invention provides that the monoclonal antibody or functional fragment thereof is a non-competitive inhibitor of plasmin activity.

In embodiments, the invention provides that the monoclonal antibody or functional fragment thereof requires loops four and five of plasmin to mediate binding of the monoclonal antibody to plasmin. In embodiments, the invention provides that the monoclonal antibody or functional fragment thereof requires loop 7 of plasmin to mediate binding of the monoclonal antibody to plasmin.

In embodiments, the invention provides that the monoclonal antibody or functional fragment thereof does not specifically bind non-plasmin serine-proteases trypsin, thrombin, activated protein C, kallikrein, neutrophil elastase, or a combination thereof.

In embodiments, the invention provides that the monoclonal antibody of functional fragment thereof comprises light and heavy chain variable region amino acid sequences at least 80%, 85%, 90%, 95%, 98%, and 100% identical to SEQ ID NOS:15 and 16.

In embodiments, the invention provides that the monoclonal antibody or functional fragment thereof comprises CDR amino acid sequences at least 80%, 85%, 90%, 95%, 98%, and 100% identical to amino acid sequences of SEQ ID NOS:9-14.

In embodiments, the invention provides a method of inhibiting plasmin activity or a method of treating hemorrhage in a subject in need thereof a monoclonal antibody or functional fragment thereof comprises amino acid sequences selected from those presented in Tables 1A and 1B, Tables 2A and 2B, and FIGS. 6A-6D.

The invention provides a pharmaceutical composition for inhibiting plasmin activity or treating hemorrhage comprising a therapeutically effective amount of an antifibrinolytic composition comprising the plasmin-specific monoclonal antibody or functional fragment thereof and a pharmaceutically acceptable carrier. The invention provides a partially isolated antibody comprising the features described herein.

BRIEF DESCRIPTION OF THE DRAWINGS

FIG. 1A shows Pi binds specifically to the protease domain of reduced human plasmin by immunoblotting. Relative migration of molecular standards (kDa) is shown. FIG. 1B shows a ribbon diagram of microplasminogen showing the loops of the plasmin protease domain (PDB entry 1QRZ) visualized with iCN3D (https://www.ncbi.nlm.nih.gov/Structure/icn3d/icn3d.html). FIG. 1C shows binding of Pi to various plasmin protease loop mutants. Wells of a microtiter plate were coated with native (wild-type, WT) or various microplasmin loop mutants (5 ug/ml). After blocking, Pi, a polyclonal rabbit anti-plasmin (plasmin Ab) or a non-reactive mouse (anti-digoxin, control) antibody (1 ug/ml) were added to wells. The bound antibodies (Pi, control) were detected by a secondary anti-mouse peroxidase (1:10,000) and the plasmin antibodies were detected by anti-rabbit peroxidase antibody (1:5,000) followed by TMB substrate with monitoring at A405. FIG. 1D shows relative binding affinity or avidity of Pi to human plasminogen. Wells of microtiter plate were coated with human plasminogen (2 ug/ml). After blocking and washing, various concentrations of purified Pi (shown) were added for 1 h. After washing the amount of antibody bound was detected by a secondary anti-mouse antibody followed by TMB substrate with monitoring at A405 nm. Data shown the means±SE of triplicate observations, experiments repeated at least twice. The data were analyzed with Graphpad Prism, r=0.95.

FIG. 2A shows human plasmin (2.8 nM) was mixed with S2251 substrate and Pi ($1 \times 10^{-9}$ to $3.3 \times 10^{-8}$ M) or EACA ($3.9 \times 10^{-3}$ to $0.25 \times 10^{-1}$ M) or no inhibitor, and the rate of substrate cleavage was monitored at A405 nm for 20 min. The percent residual activity of plasmin as a function of the log concentration of inhibitor is shown. FIG. 2B shows effect of Pi on velocity of substrate cleavage by human plasmin. Human plasmin (100 nM, Hematologic Technologies, Inc.) was mixed with or without Pi (50 nM) in the presence of the substrate S2251 (0.1 to 4 mM). The initial rate of substrate cleavage (6 min.) was monitored at A405. Data were plotted and analyzed using Michaelis-Menten kinetics by the Graphpad Prism Program. Means (duplicate observations) are shown and are representative of 4 separate experiments. FIG. 2C shows comparative inhibition of human plasmin by a2AP and P. Human plasmin (200 nM) was mixed with a2AP (12.5 to 200 nM) or Pi (15.625 to 500 nM) or no inhibitor and the cleavage of S2251 was monitored at A405. The means of duplicate observations are shown. FIG. 2D shows fab and chimeric Fab forms of Pi efficiently inhibit plasmin enzymatic activity. Plasmin (25 nM) was mixed with various concentrations (0-200 nM) of mouse Fab or chimeric Fab (cFab) and S2251 (0.5 mM) in TBS buffer pH 7.4. Plasmin activity was measured by the release of paranitroanilide product at A405 over time.

FIG. 3A shows binding of Pi to various serine proteases. The binding of Pi or a control monoclonal antibody (anti-digoxin, Ctl) to human (h) plasminogen (Pg), mouse (m) Pg, tissue plasminogen activator (tPA), trypsin (tryps.), chymotrypsin (chym.) or bovine serum albumin (was assessed in microtiter plates by an ELISA as described in Methods. Effect of Pi or no Pi on plasmin activity generated in various animal plasmas after the addition of urokinase. Plasmin activity in human (Hu), dog, guinea pig (GP), bovine (Bov), cat (Cat), gerbil (Ger), hamster (Ham), pig, rabbit (Rab) and rat plasmas was assessed after addition of urokinase (UK) by the cleavage of S2251 substrate as described in Methods. The effect of various concentrations of Pi (0-2000 nM) on clots formed with human, baboon or African green monkey plasmas. Clot lysis was measured in microtiter plates after addition of urokinase as described in Methods. FIG. 3D shows comparative clot dissolution by two different anti-catalytic antibodies, Pi MAb38 and PiMAb340, which bind to different epitopes of the plasmin protease domain.

FIG. 4A shows effect of EACA and Pi on plasmin-mediated cleavage of factor V. Human factor V (2 ug) was mixed with EACA (1 mM), a control monoclonal antibody (CTL, anti-digoxin, 5 ug) or Pi (5 ug) for 1 hr at room temperature, followed by SDS-PAGE on 7.5% gels. The relative migration of molecular weight standards is shown (kDa). Closed arrow heads indicate uncleaved factor V, open arrowheads indicated cleaved factor V. FIG. 4B shows comparative, dose-related effects of EACA and Pi on human clot lysis. Human plasma was clotted with CaCl2 (10 mM) and thrombin (1 U/ml) in the presence of trace amounts of 125I fibrinogen for 1 h at 37 deg. C. After washing in 1 ml of TBS pH 7.4, tPA (5 nM) was added in the presence of various amounts of Pi (62.5 to 1000 nM), EACA (0.125 mM to 2 mM) or no inhibitor. After 2.5 h the amount of fibrinolysis was determined by measuring the amount of 125I-fibrin dissolved in the supernatant. Means of duplicate observations are shown. FIG. 4B shows a2AP vs. Pi. Clots were formed as above in the presence of human plasminogen (2 uM) and a2AP (1 uM) or Pi (1 uM) and various amounts of tPA (0-10 nM). Clot dissolution was monitored in duplicate over 2 h in microtiter plate wells at A405 nm. The amount of fibrinolysis was determined by the relative decrease in A405 as described in Methods.[35] FIG. 4D shows comparative effect of different Pi molecular forms on dissolution of human clots. Human plasma clots were mixed with various concentrations of Pi IgG, Pi Fab and chimeric Pi Fab (25 nM-400 nM) and plasmin was activated by urokinase. The amount of clot lysis was determined as described in Methods.

FIG. 5A shows duration of tail bleeding. FIG. 5B shows blood loss from bleeding. Anesthetized mice were treated in a randomized, blinded fashion with saline (Control), Pi (100 nmole/kg) or EACA (510 micromole/kg) intravenously. Human plasminogen (100 nmole/kg) and plasminogen activator (80,000 IU/kg) were given over 60 min. Tail bleeding was initiated 40 min. after the infusion. Tails were pre-warmed for 5 mins in 3 mL of 37° C. saline and bleeding was monitored as described.36,37 N=5-6, Means±SE are shown. *p<0.05, **p<0.01; ns, not significant. Kruskal Wallis one way ANOVA, Dunn's corrections.

FIGS. 6A-6D show Clothia sequence numbering of variable sequences of Pi light chain (FIG. 6A, SEQ ID NO:15) and heavy chain (FIG. 6B, SEQ ID NO:16). The CDR loops for the light chain (FIG. 6C, SEQ ID NO:15 and SEQ ID NOS:9-11) (blue and two shades of green greyscales) and heavy chain (FIG. 6D, SEQ ID NO:16 and SEQ ID NOS:12-14) (red, orange and purple greyscales) are shown. Produced on IMGT/DomainGapAlign Program version: 4.9.2 (2016-09-26) Ehrenmann F., Kaas Q. and Lefranc M.-P. Nucleic Acids Res., 38, D301-307 (2010). PMID: 19900967.

DETAILED DESCRIPTION

Figure 1A:
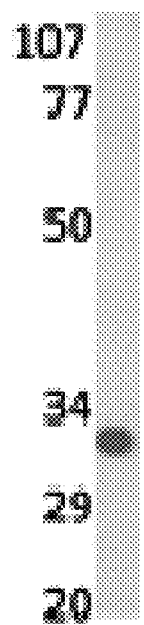
FIGS. 1A-1D show binding specificity and avidity of Pi for human plasmin.

This disclosure provides antibodies and other binding molecules directed against unique loop structures in the plasmin protease domain, which act as a highly specific inhibitor of plasmin-mediated fibrinolysis in vitro and surgical bleeding in vivo.

In embodiments, the invention provides a method of inhibiting plasmin activity in a subject in need thereof comprising administering to the subject an effective amount of a plasmin inhibiting composition comprising a plasmin protease domain-specific monoclonal antibody or functional fragment thereof.

In embodiments, the invention provides a method of treating hemorrhage in a subject in need thereof comprising administering to the patient an effective amount of a pharmaceutical composition comprising a plasmin protease domain-specific monoclonal antibody or functional fragment thereof and a pharmaceutically acceptable excipient.

In embodiments, the invention provides that the monoclonal antibody or functional fragment thereof inhibits fibrinolysis. In embodiments, the invention provides that the monoclonal antibody or functional fragment thereof inhibits plasmin cleavage of Factor V protein. In embodiments, the invention provides that the monoclonal antibody or functional fragment thereof inhibits plasmin cleavage of tripeptide paranitroanilide substrate more potently than epsilon amino caproic acid.

In embodiments, the invention provides the subject is a human. In embodiments, the invention provides that the monoclonal antibody or functional fragment thereof is a non-competitive inhibitor of plasmin activity.

In embodiments, the invention provides that the monoclonal antibody or functional fragment thereof requires loops four and five of plasmin to mediate binding of the monoclonal antibody to plasmin. In embodiments, the invention provides that the monoclonal antibody or functional fragment thereof requires loop 7 of plasmin to mediate binding of the monoclonal antibody to plasmin.

In embodiments, the invention provides that the monoclonal antibody or functional fragment thereof does not specifically bind non-plasmin serine-proteases trypsin, thrombin, activated protein C, kallikrein, neutrophil elastase, or a combination thereof.

In embodiments, the invention provides that the monoclonal antibody of functional fragment thereof comprises light and heavy variable region amino acid sequences at least 80%, 85%, 90%, 95%, 98%, and 100% identical to SEQ ID NOS:15 and 16.

In embodiments, the invention provides that the monoclonal antibody or functional fragment thereof comprises CDR amino acid sequences at least 80%, 85%, 90%, 95%, 98%, and 100% identical to amino acid sequences of SEQ ID NOS:9-14.

In embodiments, the invention provides a method of inhibiting plasmin activity or a method of treating hemorrhage in a subject in need thereof a monoclonal antibody or functional fragment thereof comprises amino acid sequences at least 80%, 85%, 90%, 95%, 98%, and 100% identical to amino acid sequences selected from those presented in Tables 1A and 1B, Tables 2A and 2B, and FIGS. 6A-6D.

The invention provides a pharmaceutical composition for inhibiting plasmin activity or treating hemorrhage comprising a therapeutically effective amount of an antifibrinolytic composition comprising the plasmin-specific monoclonal antibody or functional fragment thereof and a pharmaceutically acceptable carrier. The invention provides an at least partially isolated monoclonal antibody or a functional fragment thereof comprising the features described herein.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

It is understood that aspects and embodiments of the invention described herein include "consisting" and/or "consisting essentially of" aspects and embodiments.

Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

As used herein, "antibody" refers to an intact immunoglobulin (Ig) molecule of any isotype, or an immunologically active fragment thereof that can compete with the intact antibody for specific binding to the target antigen. In some instances, the antibody is an immunological fragment of an intact antibody (e.g., a $F_{ab}$, a $F_{ab'}$, a $F_{(ab')2}$, or a single-chain Fv fragment scFvs). Antibodies include, but are not limited to, monoclonal antibodies, polyclonal antibodies, bispecific antibodies, minibodies, domain antibodies, synthetic antibodies, chimeric antibodies, humanized antibodies, human antibodies, antibody fusions, and fragments thereof, respectively. An intact antibody will generally comprise at least two full-length heavy chains and two full-length light chains, but in some instances can include fewer chains such as antibodies naturally occurring in camelids which can comprise only heavy chains. Antibodies can be derived solely from a single source, or can be "chimeric," that is, different portions of the antibody can be derived from two different antibodies. The basic antibody structural unit typically comprises a tetramer. Each such tetramer typically is composed of two identical pairs of polypeptide chains, each pair having one full-length "light" (about 25 kDa) and one full-length "heavy" chain (50-70 kDa). The amino-terminal portion of each chain typically includes a variable region of about 100 to 110 or more amino acids that typically is responsible for antigen recognition. The carboxy-terminal portion of each chain typically defines a constant region that can be responsible for effector function. Human light chains are typically classified as kappa and lambda light chains. Heavy chains are typically classified as mu, delta, gamma, alpha, or epsilon, and define the antibody's isotype as IgM, IgD, IgG, IgA, and IgE, respectively. Certain classes such as IgG and IgM have subclasses as well (e.g. $IgG_1$, $IgG_2$, $IgG_3$, $IgG_4$, and so forth).

As used herein, "monoclonal antibody" or "MAb" refers to a population of antibodies that are made by identical immune cells that are all clones of a unique parent cell.

As used herein, "antigen binding region" refers the part of an antibody molecule that contains the amino acid residues that interact with an antigen and confer on the antibody molecule its specificity and affinity for the antigen. An antigen binding region typically includes one or more "complementary binding regions" ("CDRs"). A "CDR" is an amino acid sequence that contributes to antigen binding specificity and affinity. Certain antigen binding regions also include one or more "framework" regions. "Framework" regions can aid in maintaining the proper conformation of the CDRs to promote binding between the antigen binding region and an antigen. Structurally, framework regions can be located in antibodies between CDRs.

As used herein, "epitope" refers to a region of an antigen that is bound by an antibody that targets that antigen, and typically includes specific amino acids that directly contact the antibody. Generally, antibodies specific for a particular target antigen will preferentially recognize an epitope on the target antigen in a complex mixture of proteins and/or macromolecules.

As used herein, "immunological binding," refers to the non-covalent interactions of the type which occur between an antibody molecule and an antigen for which the antibody is specific. The strength, or affinity, of immunological binding interactions can be expressed in terms of a dissociation constant ($K_d$) of the interaction, wherein a smaller $K_d$ represents a greater affinity. Immunological binding properties of selected antibodies can be quantified using methods well known in the art. One such method entails measuring the rates of antigen-binding site/antigen complex formation and dissociation wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. The ratio of $K_{off}/K_{on}$ enables the cancellation of all parameters not related to affinity, and is equal to the dissociation constant $K_d$. An antibody of the present disclosure is said to specifically bind its target antigen when the dissociation constant ($K_d$) is ≤1 µM. An antibody of the present disclosure specifically binds antigen with "high affinity" when the $K_d$ is ≤5 nM, and with "very high affinity" when the $K_d$ is ≤0.5 nM.

Variations in the amino acid sequences of antibodies are contemplated as being encompassed by the present disclosure, providing that the variations in the amino acid sequence maintain at least 75%, more preferably at least 80%, 90%, 95%, and most preferably 99% sequence identity. Certain percentages in between are included, such as 75%, 76%, 77%, 78%, 79% 80%, 81%, 82%, 83%, 84%, 85%, 86%, 87%, 88%, 89%, 90%, 91%, 92%, 93%, 94%, 95%, 96%, 97%, 98%, and 99% sequence identity. In particular, conservative amino acid replacements are contemplated. Conservative replacements are those that take place within a family of amino acids that are related in their side chains. Genetically encoded amino acids are generally divided into families: (1) acidic amino acids are aspartate, glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, proline, tryptophan, tyrosine and valine. Other families of amino acids include (i) serine and threonine, which are the aliphatic-hydroxy family; (ii) asparagine and glutamine, which are the amide containing family; (iii) alanine, valine, leucine and isoleucine, which are the aliphatic family; and (iv) phenylalanine, tryptophan, and tyrosine, which are the aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional antibody can readily be determined by assaying the specific activity of the antibody derivative. Fragments or analogs of antibodies can be readily prepared by those of ordinary skill in the art. Preferred amino- and carboxy-termini of fragments or analogs occur near boundaries of functional domains.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such antibodies. Antibodies can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence).

As used herein, "substantially pure" means an object species is the predominant species present (i.e., on a molar basis it is more abundant than any other individual species in the composition), and preferably a substantially purified fraction is a composition wherein the object species comprises at least about 50% (on a molar basis) of all macromolecular species present. Generally, a substantially pure composition will comprise more than about 80% of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

As used herein, "patient" and "subject" are used interchangeably and include human and veterinary subjects.

As used herein, "target antigen" refers to a molecule or a portion of a molecule capable of being selectively bound by an antibody. In certain embodiments, a target can have one or more epitopes. In this context, it does not require that the molecule be foreign or that it be capable of inducing an immune response.

As used herein, "pharmaceutical agent composition" (or agent or drug) refers to a chemical compound, composition, agent or drug capable of inducing a desired therapeutic effect when properly administered to a patient. It does not necessarily require more than one type of ingredient.

As used herein, "pharmaceutically acceptable carrier" refers to an excipient, diluent, preservative, solubilizer, emulsifier, adjuvant, and/or vehicle with which an active agent is administered. Such carriers may be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose may also be a carrier. Methods for producing compositions in combination with carriers are known to those of skill in the art. In some embodiments, the language "pharmaceutically acceptable carrier" is intended to include any and all solvents, dispersion media, coatings, isotonic and absorption delaying agents, and the like, compatible with pharmaceutical administration. The use of such media and agents for pharmaceutically active substances is well known in the art.

As used herein, "therapeutically effective amount" refers to the amount of an antibody determined to produce a therapeutic response in a patient. Such therapeutically effective amounts are readily ascertained by one of ordinary skill in the art.

As used herein, "modulator," refers to a composition that changes or alters the activity or function of a molecule. For example, a modulator can cause an increase or decrease in the magnitude of a certain activity or function of a molecule compared to the magnitude of the activity or function observed in the absence of the modulator. In certain embodiments, a modulator is an inhibitor, which decreases the magnitude of at least one activity or function of a molecule. Certain exemplary activities and functions of a molecule include, but are not limited to, binding affinity, enzymatic activity, and signal transduction.

As used herein, "treat" and "treatment" include therapeutic treatments, prophylactic treatments, and applications in which one reduces the risk that a subject will develop a disorder or other risk factor. Treatment does not require the complete curing of a disorder and encompasses embodiments in which one reduces symptoms or underlying risk factors.

As used herein, "prevent" does not require the 100% elimination of the possibility of an event. Rather, it denotes that the likelihood of the occurrence of the event has been reduced in the presence of the compound or method.

EXAMPLES

In some exemplary embodiments, a monoclonal antibody was generated against unique sequences in the solvent-exposed, surface loops of the plasmin protease domain. This plasmin inhibitor (Pi) was up to seven logs more potent than EACA for neutralizing plasmin cleavage of small molecular substrates and ~5000-fold more potent for quenching fibrinolysis. When compared to a2-antiplasmin, the most potent covalent inhibitor of plasmin, the Pi was similarly effective for blocking plasmin catalysis of a small molecular substrate and more potent for inhibiting fibrinolysis. This Pi was exquisitely specific by comparison to other inhibitors; it required loops 4 and 5 of human plasmin for binding and it neutralized plasmin activity in human plasma, but not in plasma from nine other species. Enzymatic analysis indicated that the Pi functions as a non-competitive inhibitor. Fab or chimerized Fab fragments of the Pi were equivalently effective for reducing plasmin catalysis and fibrinolysis. In vivo, in a humanized model of fibrinolytic surgical bleeding, the Pi was more effective at reducing bleeding than a clinical dose of EACA. The data shows that the exemplary monoclonal antibody Pi, directed to unique loop sequences in the protease domain, is an exquisitely specific, highly potent, non-competitive plasmin inhibitor, which significantly reduces experimental surgical bleeding in vivo. The improved specificity and potency of this Pi may translate into a more effective approach to serious, life-threatening bleeding. The ultra-potent and specific monoclonal antibody Pi does not significantly cross the blood brain barrier or placenta, and is not excreted by the kidney. By virtue of these properties, this Pi can help remedy the limitations in the current treatment of severe hemorrhage associated with fibrinolysis.

Methods

Monoclonal antibody generation. Monoclonal antibodies were generated by somatic cell fusion as described using the cells from mice immunized four times over eight months with human plasmin protease domain coupled to aprotinin agarose.[19] Direct binding assays were performed to identify mice with the highest titer of antibody binding to the human plasminogen protease domain. Mice were hyper-immunized intraperitoneally with the human plasminogen protease domain (50 ug) pre-activated with urokinase (100 U, 30 min.). After euthanasia, immune splenocytes were fused with SP2/0 cells with polyethylene glycol as described.[19] Fused cells were cultured in hypoxanthine aminopterin and thymidine selection medium at 37° C. in 5% $CO_2$ atmosphere. Clones were selected by a radioimmunoassay in which microtiter plate were coated with goat-anti-mouse Fab antibody (5 ug/ml, 25 ul) for 1 hr. Wells were blocked with 1% bovine serum albumin. Hybridoma supernatants were added and plates were incubated for 1 hr at room temperature (RT). After washing, wells were incubated with $^{125}$I-human plasmin (50,000 cmp/25 ul) for 1 hr. After washing, bound $^{125}$I-human plasmin was detected by gamma scintigraphy. The positive hybridomas were subcloned by limiting dilution and stored in liquid nitrogen.

Monoclonal antibody purification. Hybridoma supernatant was applied to an anti-mouse IgG agarose column (Immunechem, Canada) with a flow speed at 1 ml/min. The column was washed with PBS pH 7.4. The antibody was eluted with 0.2M glycine, pH 2.9, followed by dialysis in PBS pH 7.4 at 4° C. overnight. The antibody was concentrated with Amicon Ultra-15 centrifugal filters (Millipore, Billerica, Mass.) according to the manufacturer. The protein concentration was determined by BCA method.

Recombinant proteins. Plasmin protease domain mutants were recombinantly expressed in E. coli as described.(9) The cDNA sequence of the Pi was isolated from hybridoma cells by PCR cloning with redundant primers. A humanized chimeric version of the Pi was expressed in HEK293 cells by transient cell transfection. After 96 hours, the suspension culture was collected. Purified chimeric Pi was purified by HiTrap rProteinG FF and passed through a 0.2 urn filter. It was provided by Translational Sciences (Memphis, Tenn.).

Saturation binding assay. Saturation binding assays were performed by ELISA in 96-well plates coated with 2 ug/ml of plasmin or plasminogen at room temperature for 1 hour. Wells were washed with PBS-T: (10 mM phosphate buffer pH 7.4, 150 mM NaCl, 0.05% Tween 20) six times. Non-specific protein binding sites were blocked with 1% BSA for 1 hour at room temperature. After washing the plate as above, various concentrations of antibody (0.002 to 100 ug/ml) were added to the plate in duplicate and for 1 hour at room temperature. The plate was washed and horseradish peroxidase (HRP) conjugated goat anti-mouse secondary antibody (1:8000, Santa Cruz, Dallas, Tex.) was added to the plate. After 1 hour incubation at room temperature, the plate was washed and TMB was added. The absorbance was then read at 370 nm.

Specificity of Pi binding. The binding of the Pi to different serine proteases was assessed by ELISA in 96-well plates coated with human plasminogen, mouse plasminogen, tPA, trypsin or chymotrypsin (10 ug/ml) and blocked with 1% BSA. After incubation and washing, Pi or control monoclonal antibody supernatants (anti-digoxin) were added to the wells for 1 h in triplicate. Then goat anti mouse antibody conjugated with HRP (1:5000, Sc-2005, Santa Cruz) was then added. The plate was washed after incubation for 1 h. TMB was added to the wells and absorbance at 370 nm was recorded.

Plasmin inhibition analysis. Human plasmin (2.8 nM) was mixed with S2251 substrate and Pi ($1\times10^{-9}$ to $3.3\times10^{-8}$M) or EACA ($3.9\times10^{-3}$ to $0.25\times10^{-1}$M) or no inhibitor, and the rate of substrate cleavage was monitored by the release of paranitroanilide product at A405 nm for 20 min. The percent residual activity of plasmin as a function of the log concentration of inhibitor was determined.

The effect of Pi on the velocity of substrate cleavage by human plasmin was examined. Human plasmin (100 nM, Hematologic Technologies, Inc.) was mixed with or without Pi (50 nM) in the presence of the substrate S2251 (0.1 to 4 mM). The initial rate of substrate cleavage (6 min.) was monitored at A405. Data were plotted and analyzed using Michaelis-Menten kinetics by the Graphpad Prism Program.

The inhibition of human plasmin by a2AP and Pi was compared. Human plasmin (200 nM) was mixed with a2AP (12.5 to 200 nM) or Pi (15.625 to 500 nM) or no inhibitor and the cleavage of S2251 was monitored at A405 in duplicate.

The effects of mouse or chimeric Fab on plasmin activity were examined. Plasmin (25 nM) was mixed with various concentrations (0-200 nM) of mouse Fab or chimeric Fab (cFab) and S2251 (0.5 mM) in TBS buffer pH 7.4. Plasmin activity was measured by the release of paranitroanilide product at A405 over time.

Specificity of plasmin inhibition. The effect of the Pi on different animal plasmins was examined after addition of the plasminogen activator urokinase. Various animal plasmas (5 ul) were mixed in microtiter plates in the presence of Pi (1 uM, 10 ul) or buffer, S2251 (10 ul, 0.5 mM final), urokinase (100 or 200 U) in a total volume of 100 ul with PBS. The plates were incubated at 37 deg. C. and the rate of plasmin generation was monitored by substrate cleavage at 405 nm for 1 hr.

Factor V cleavage. Human factor V (2 ug, IHFV, Innovative Research) was mixed with plasmin (0.05 ug) for 1 hr at RT in the presence of EACA (1 mM), Pi (5 ug) or a control monoclonal antibody (digoxin, 5 ug). Samples were then subjected to SDS-PAGE under reducing conditions on 7.5% gels. Protein bands were detected by staining with Coomassie blue dye.

Fibrinolytic assays in vitro. The effects of EACA vs. Pi on fibrinolysis were examined in duplicate in human plasma clotted with CaCl2 (10 mM) and thrombin (1 U/ml) in the presence of trace amounts of $^{125}$I fibrinogen for 1 h at 37 deg. C. After washing in 1 ml of TBS pH 7.4, tPA (5 nM) was added in the presence of various amounts of Pi (62.5 to 1000 nM), EACA (0.125 mM to 2 mM) or no inhibitor. After 2.5 h the amount of fibrinolysis was determined by measuring the amount of $^{125}$I-fibrin dissolved in the supernatant.

The effects of a2AP and Pi on fibrinolysis were examined in clots were formed as above in the presence of human plasminogen (2 uM) and a2AP (1 uM) or Pi (1 uM) and various amounts of tPA (0-10 nM). Clot dissolution was monitored in duplicate over 2 h in microtiter plate wells at A405 nm. The amount of fibrinolysis was determined by the relative decrease in A405 as described. (26)

The ability of Pi to inhibit primate clot lysis was also examined in a microtiter plate assay. Human, baboon or African green monkey plasma (5 ul) was added to 96-well plates in the presence of various concentrations of Pi (0-2000 nM), CaCl2 (2 mM), thrombin (0.125 U/ml) and human fibrinogen (2 mg/ml) and urokinase (10 U). The wells were incubated at 37° C., clot lysis was recorded kinetically for 120 min. and the time required for complete clot lysis was recorded.

The effects of Pi IgG, Fab or chimeric Fab were also compared in a clot lysis assay in microtiter plates. Human plasma (5 ul) was mixed with Pi (IgG or Fab, 0-400 nM), fibrinogen (2 mg/ml), CaCl2 (2 mM), thrombin (0.125 U/ml) and urokinase (10 U) in a total volume of 80 ul. Clot dissolution at 37 deg. C. was monitored at 405 nm. The percent clot dissolution at 30 min. was determined as the percent change in peak turbidity from baseline=100%×(peak absorbance−30 min. absorbance)/(peak absorbance−baseline absorbance).

The comparative effects of Pi, MAb 340 and a control MAb (anti-digoxin) were examined in a clot lysis assay in microtiter plates. Human plasma (50 ul) was mixed with the MAbs (20 ug) in duplicate and then clotted with CaCl2 and thrombin, with or without recombinant (r)-tPA (2 nm). Clot dissolution at 37 deg. C. was monitored at 405 nm for 120 min. The time required to fully dissolve the clots during the 120 min. observation period was recorded. Clots incubated with r-tPA and MAb 340 or the Pi did not significantly dissolve. ***$p<0.001$ vs. time for clot dissolution in samples with the control MAb or no MAb.

Fibrinolytic bleeding assays in vivo. Anesthetized mice were treated in a randomized, blinded fashion with saline (Control), Pi (100 nmole/kg) or EACA (510 micromole/kg). Human plasminogen (100 nmole/kg) and plasminogen activator (80,000 IU/kg) were given over 60 min. Tail bleeding started 40 min. after the infusion. Tails were pre-warmed for 5 mins in 3 mL of 37° C. saline as described.(27, 28).

Statistical analyses. Data are shown as mean±standard error. Saturation binding and velocity vs. substrate curves were analyzed by nonlinear regression using a one-site binding hyperbole and Michaelis-Menten kinetic models with the aid of GraphPad Prism. In vivo bleeding data was analyzed by a non-parametric, Kruskal Wallis one way ANOVA with Dunn's correction. A $p<0.05$ was considered significant.

Results

Figure 1B:
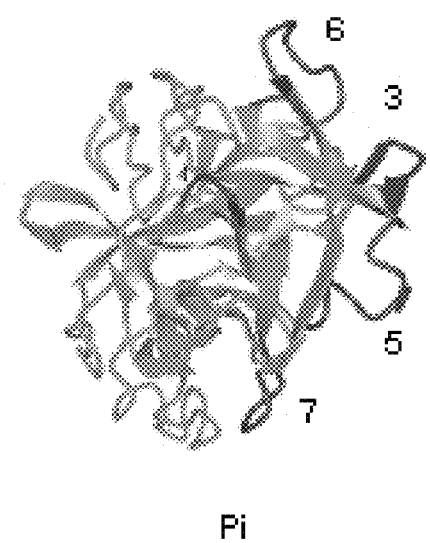
Figure 1C:
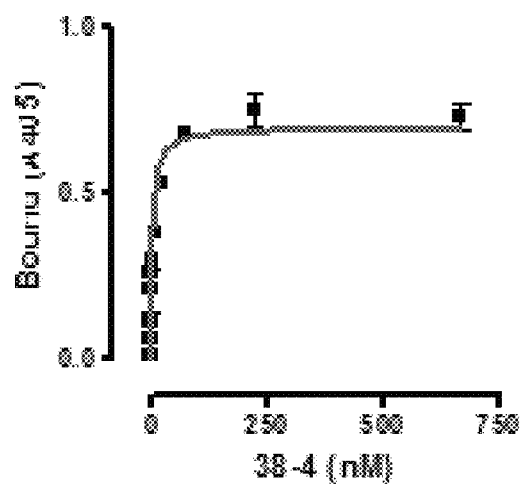
Figure 1D:
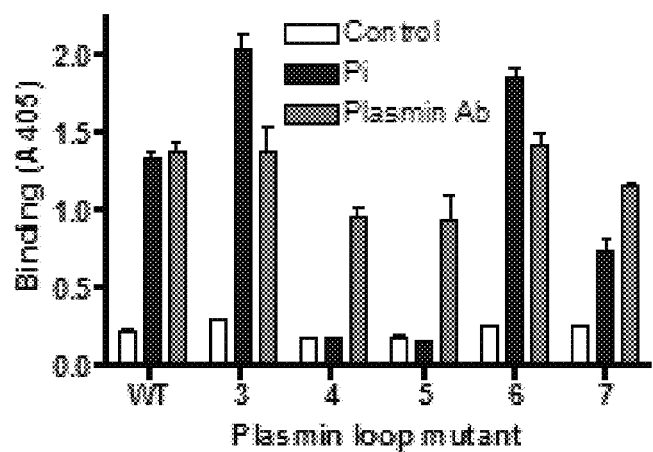

A monoclonal antibody plasmin inhibitor (Pi) directed against specific protease domain loops. A monoclonal antibody plasmin inhibitor (Pi) was generated that bound specifically to the protease domain of plasmin (microplasmin), as indicated by immunoblotting (FIG. 1A). Although the core protease structure is highly conserved among serine proteases, the external loop structures of plasmin (FIG. 1B) differ significantly from other enzymes and have been shown to mediate specific interactions of plasmin with substrate modifiers (such as streptokinase), substrates and inhibitors (FIG. 1B) (9). Binding studies with different plasmin mutants, in which the loop structures of plasmin were altered, showed that the Pi binds to an epitope in the protease domain (FIG. 1B) that requires native loops 4 and 5, but does not require the native sequences of loops 3, 6 or 7 (FIG. 1C). This Pi bound plasminogen with high avidity ($K_d$3.4±0.8 nM, FIG. 1D) suggesting that it will be fully bound at normal physiologic concentrations of plasminogen.

Figure 2A:
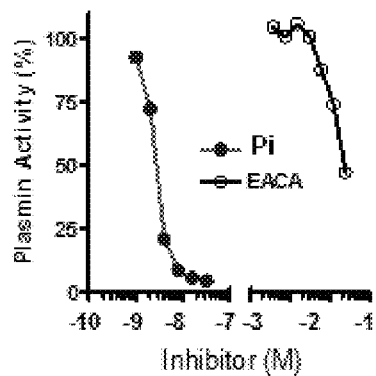
FIGS. 2A-2D show comparative inhibition of plasmin activity by Pi EACA and a2AP.
Figure 2B:
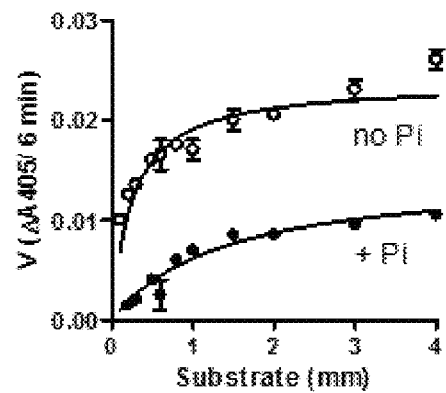
Figure 2C:
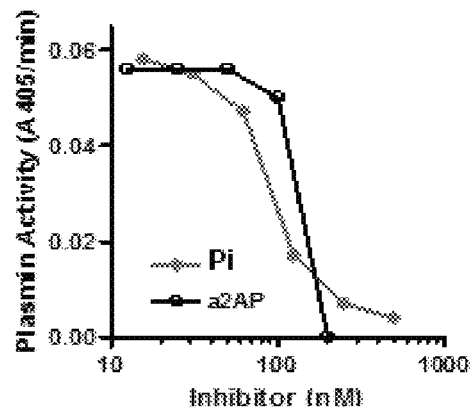
Figure 2D:
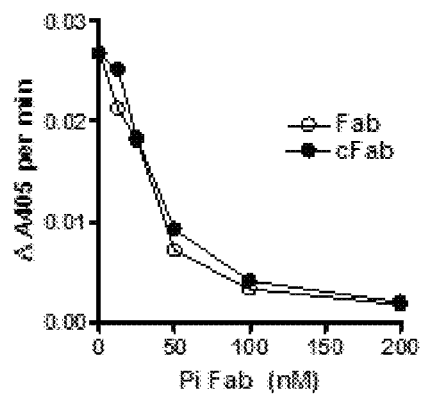
Figure 3A:
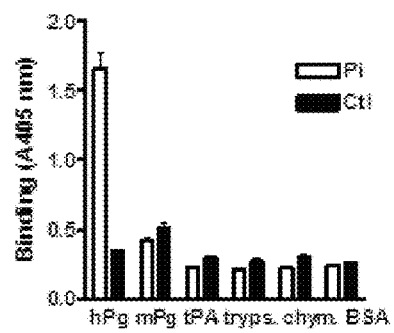
FIGS. 3A-3D show binding and inhibitory specificity of Pi.
Figure 3B:
Figure 3C:
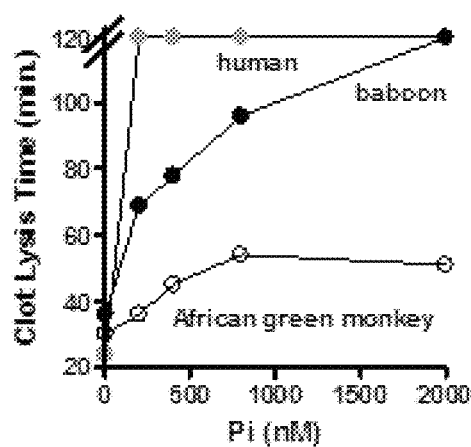

The Pi is a potent non-competitive inhibitor of plasmin catalytic function with small substrates. The Pi potently neutralized plasmin-mediated cleavage of a small tripeptide paranitroanilide substrate (S2251) with ~7 logs greater potency than EACA (FIG. 2B). The Pi reduced the Vmax of plasmin cleavage of S2251, suggesting that it acted largely as a non-competitive inhibitor of plasmin activity (FIG. 2B). When compared to a2-antiplasmin, the most potent, covalent inhibitor of plasmin, the Pi had similar potency for inhibiting plasmin cleavage of S2251 (FIG. 3C). To determine whether the Fc region of the MAb resulted in steric hindrance or affected the inhibitory function of the Pi, the effects of Fab fragments of the Pi, which lacked the Fc domain, were examined. The cDNA sequence for the Pi was obtained by PCR cloning with redundant primers (Table 1). Both the mouse Fab and the chimeric, recombinantly expressed Fab forms of the Pi potently inhibited plasmin activity with the tripeptide substrate (FIG. 2D), indicating that steric effects by the larger IgG molecule did not contribute significantly to blocking plasmin activity.

Figure 3D:
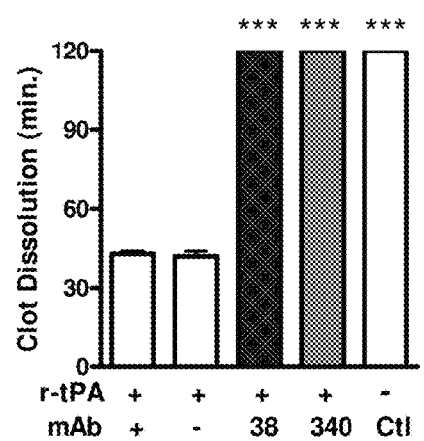

Comparative specificity of the Pi. To determine the specificity of the Pi, we examined its binding to other serine proteases. By comparison to a control (anti-digoxin) monoclonal antibody, the Pi showed no specific binding to mouse plasminogen, human tPA, trypsin, chymotrypsin or bovine serum albumin (control) (FIG. 3A). The effects of the Pi on plasmin was studied in several different animal plasmas. The Pi suppressed plasmin in human plasma generated by urokinase, but the Pi did not inhibit plasmin activity in dog, guinea pig, bovine, cat, gerbil, hamster, pig, rabbit or rat plasma (FIG. 3B). Non-human primate plasmin has the greatest homology with human plasmin. The Pi markedly prolonged plasmin-induced fibrinolysis of human clots and also showed dose-related suppression of baboon and African green monkey clots (FIG. 3C). These data show that the Pi specifically inhibits human and non-human primate plasmin and does not affect non-primate plasmins or bind to other serine proteases. FIG. 3D shows comparative clot dissolution by two different anticatalytic antibodies, Pi MAb38 and PiMAb340, which bind to different epitopes of the plasmin protease domain.

Generation of other Pis directed to the plasmin protease domain. To examine the generalizability of this approach, other monoclonal antibodies specifically generated against the plasmin protease domain were tested. MAb 340, which binds to a different epitope than Pi (i.e., requiring loop 7), also inhibited human clot lysis initiated by r-tPA, whereas as a control (anti-digoxin) MAb did not (FIG. 3D).

Figure 4A:
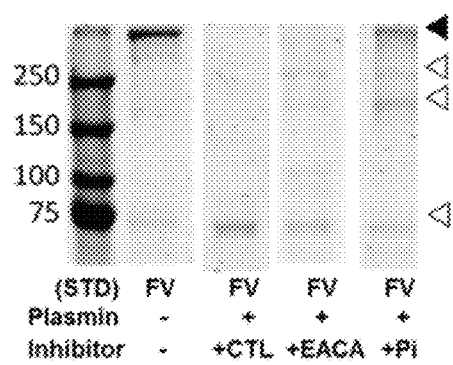
FIGS. 4A-4D show comparative inhibition of factor V cleavage and human clot fibrinolysis (dissolution) by Pi, EACA and a2AP.
Figure 4B:
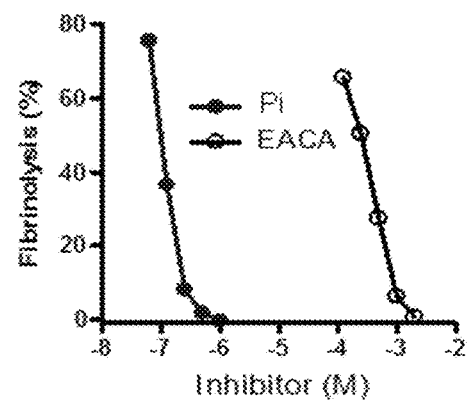
Figure 4C:
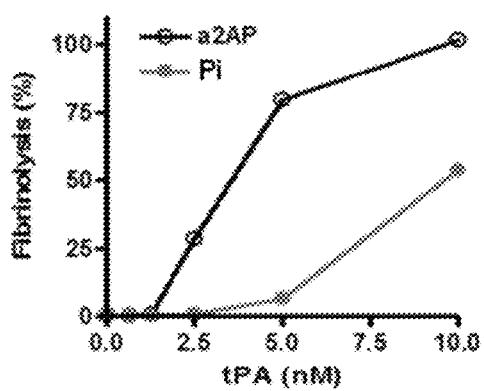
Figure 4D:
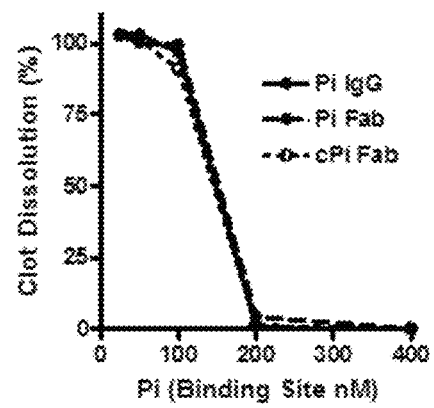

Comparative inhibition of factor V cleavage and fibrinolysis. In vivo, factor V cleavage by plasmin is a hallmark of unregulated blood plasmin levels. In vitro, plasmin readily cleaved factor V to low molecular weight bands (FIG. 4A) in the presence of a control (anti-digoxin antibody). Therapeutic levels of EACA (1 mM) slightly diminished Factor V cleavage (FIG. 4A). However, in the presence of the Pi, Factor V cleavage was attenuated (FIG. 4A). The Pi also significantly suppressed plasmin-mediated fibrinolysis of human fibrin clots in a dose-related fashion (FIG. 4B). EACA also diminished fibrinolysis, but by comparison EACA was approximately 5,000-fold less potent than the Pi (FIG. 4B). When compared to a2-antiplasmin at the same dose, the Pi was 2-3-fold more potent in suppressing the plasmin-mediated dissolution of human fibrin clots induced by increasing doses of tPA (FIG. 4C). The whole IgG, Fab and chimeric Fab forms of the Pi effectively inhibited clot lysis with similar dose-related potency (FIG. 4D), suggesting that there are no steric effects on fibrinolysis related to the IgG molecule.

Figure 5A:
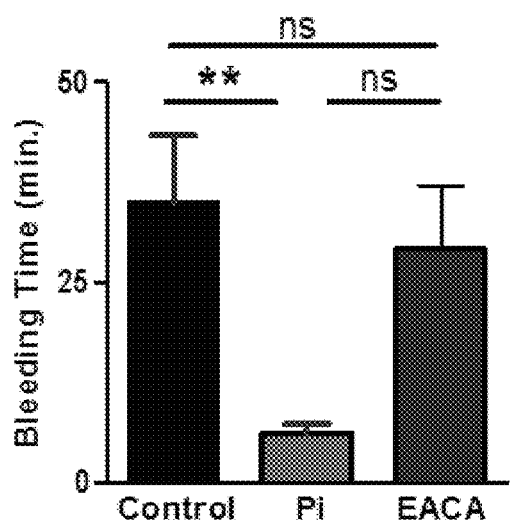
FIGS. 5A-5B show that Pi suppresses fibrinolytic bleeding in vivo.
Figure 5B:
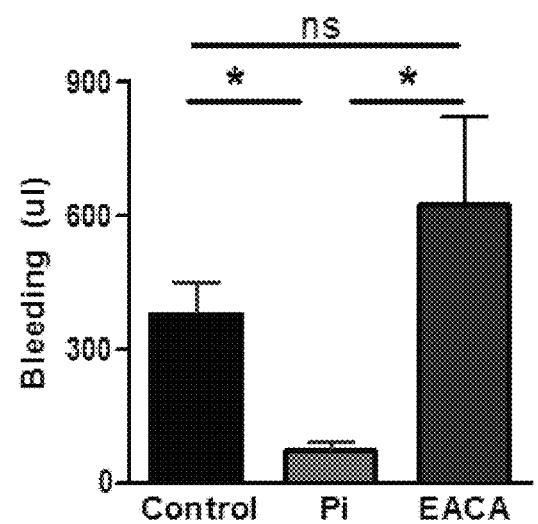

Suppression of fibrinolytic bleeding in vivo. The potential utility of the Pi for suppression of fibrinolytic bleeding was examined in vivo in randomized, blinded studies of surgical arterial and venous hemorrhage. Since the Pi specifically binds and inhibits human, but not mouse plasmin, a humanized model was developed in which mice were administered human plasminogen and human tPA.(2728) By comparison to saline (control), a clinical dose of EACA (510 micromole/kg) did not reduce bleeding time or blood loss (FIG. 5A, B). The Pi (100 nmole/kg) markedly suppressed bleeding time (>80%, $p<0.01$, FIG. 5A) and blood loss vs. controls (FIG. 5B, >85%, $p<0.05$) or vs. EACA-treated mice (FIG. 5B, $p<0.05$).

The therapeutic value of current plasmin inhibitors for treating fibrinolytic hemorrhage is limited by lack of specificity, low potency and toxicity due to off-target effects. To address these challenges of potency and specificity, an exemplary monoclonal antibody Pi was generated against unique sequences in the surface-exposed loops of the plasmin protease domain, which have been shown to mediate interactions with substrate modifiers, inhibitors and substrates[18] By comparison to lysine analogs and to α2-antiplasmin, this Pi showed exquisitely specific, high affinity binding to the protease domain of human plasmin but not to other serine proteases. The Pi acted as a potent, noncompetitive inhibitor of plasmin-mediated proteolysis of small molecular substrates (S2251). In fibrinolysis studies, the Pi was ~7 logs more potent than EACA for inhibiting small substrate cleavage and ~5000-fold more potent for inhibiting fibrin cleavage. When compared to α2-antiplasmin, the most potent plasmin inhibitor known, the Pi was similarly effective for inhibiting plasmin cleavage of small molecular weight substrates and, it appeared more potent for inhibiting fibrinolytic activity. The Pi potently neutralized plasmin-mediated fibrinolysis in primate, but not other animal plasmas. In vivo, in a model of experimental surgical bleeding, the Pi was a more potent than clinical dose EACA for stopping fibrinolytic bleeding.

Deduced amino acid sequences of Pi. The cDNAs for Pi were obtained from cloned hybridoma cells. The HC and LC gene were amplified with degenerate mouse IgG primer pairs with the cDNA as the template.

TABLE 1A

The sequence of intact LC Pi

```
        D    I    Q    M    T    Q    S    P    S    S    L    S    A    S    L
    1 GAC  ATC  CAG  ATG  ACA  CAG  TCT  CCA  TCC  TCA  CTG  TCT  GCA  TCT  CTG
      CTG  TAG  GTC  TAC  TGT  GTC  AGA  GGT  AGG  AGT  GAC  AGA  CGT  AGA  GAC

G    G    K    V    S    I    T    C    K    A    S    Q    D    I    N
   46 GGG  GGC  AAA  GTC  TCC  ATC  ACT  TGC  AAG  GCA  AGC  CAA  GAC  ATT  AAC
      CCC  CCG  TTT  CAG  AGG  TAG  TGA  ACG  TTC  CGT  TCG  GTT  CTG  TAA  TTG

K    Y    I    S    W    Y    Q    H    K    P    G    K    G    P    R
   91 AAG  TAT  ATT  TCT  TGG  TAC  CAA  CAC  AAG  CCT  GGA  AAA  GGT  CCT  AGG
      TTC  ATA  TAA  AGA  ACC  ATG  GTT  GTG  TTC  GGA  CCT  TTT  CCA  GGA  TCC

L    L    I    H    Y    T    S    T    L    Q    P    G    I    P    S
  136 CTG  CTC  ATA  CAT  TAC  ACA  TCT  ACA  TTA  CAG  CCA  GGC  ATC  CCA  TCA
      GAC  GAG  TAT  GTA  ATG  TGT  AGA  TGT  AAT  GTC  GGT  CCG  TAG  GGT  AGT

R    F    S    G    S    G    S    G    R    D    Y    S    F    S    I
  181 AGG  TTC  AGT  GGA  AGT  GGG  TCT  GGG  AGA  GAT  TAT  TCC  TTC  AGC  ATC
      TCC  AAG  TCA  CCT  TCA  CCC  AGA  CCC  TCT  CTA  ATA  AGG  AAG  TCG  TAG

S    N    L    E    P    E    D    I    A    T    Y    Y    C    L    Q
  226 AGC  AAC  CTG  GAG  CCT  GAA  GAT  ATT  GCA  ACT  TAT  TAT  TGT  CTA  CAG
      TCG  TTG  GAC  CTC  GGA  CTT  CTA  TAA  CGT  TGA  ATA  ATA  ACA  GAT  GTC

Y    D    N    L    Y    T    F    G    G    G    T    K    L    E    I
  271 TAT  GAT  AAT  CTG  TAC  ACG  TTC  GGA  GGG  GGG  ACC  AAG  CTG  GAA  ATA
      ATA  CTA  TTA  GAC  ATG  TGC  AAG  CCT  CCC  CCC  TGG  TTC  GAC  CTT  TAT

K    R    A    D    A    A    P    T    V    S    I    F    P    P    S
  316 AAA  CGG  GCA  GAT  GCT  GCA  CCA  ACT  GTA  TCC  ATC  TTC  CCA  CCA  TCC
      TTT  GCC  CGT  CTA  CGA  CGT  GGT  TGA  CAT  AGG  TAG  AAG  GGT  GGT  AGG

S    E    Q    L    T    S    G    G    A    S    V    V    C    F    L
  361 AGT  GAG  CAG  TTA  ACA  TCT  GGA  GGT  GCC  TCA  GTC  GTG  TGC  TTC  TTG
      TCA  CTC  GTC  AAT  TGT  AGA  CCT  CCA  CGG  AGT  CAG  CAC  ACG  AAG  AAC

N    N    F    Y    P    K    D    I    N    V    K    W    K    I    D
  406 AAC  AAC  TTC  TAC  CCC  AAA  GAC  ATC  AAT  GTC  AAG  TGG  AAG  ATT  GAT
      TTG  TTG  AAG  ATG  GGG  TTT  CTG  TAG  TTA  CAG  TTC  ACC  TTC  TAA  CTA

G    S    E    R    Q    N    G    V    L    N    S    W    T    D    Q
  451 GGC  AGT  GAA  CGA  CAA  AAT  GGC  GTC  CTG  AAC  AGT  TGG  ACT  GAT  CAG
      CCG  TCA  CTT  GCT  GTT  TTA  CCG  CAG  GAC  TTG  TCA  ACC  TGA  CTA  GTC

D    S    K    D    S    T    Y    S    M    S    S    T    L    T    L
  496 GAC  AGC  AAA  GAC  AGC  ACC  TAC  AGC  ATG  AGC  AGC  ACC  CTC  ACG  TTG
      CTG  TCG  TTT  CTG  TCG  TGG  ATG  TCG  TAC  TCG  TCG  TGG  GAG  TGC  AAC
```

TABLE 1A-continued

The sequence of intact LC Pi

```
       T   K   D   E   Y   E   R   H   N   S   Y   T   C   E   A
541 ACC AAG GAC GAA TAT GAA CGA CAT AAC AGC TAT ACC TGT GAG GCC
    TGG TTC CTG CTT ATA CTT GCT GTA TTG TCG ATA TGG ACA CTC CGG

T   H   K   T   S   T   S   P   I   V   K   S   F   N   W
586 ACT CAC AAG ACA TCA ACT TCA CCC ATT GTC AAG AGC TTC AAC TGG
    TGA GTG TTC TGT AGT TGA AGT GGG TAA CAG TTC TCG AAG TTG ACC

N   E   C   (SEQ ID NO: 1)
631 AAT GAG TGT     (SEQ ID NO: 2)
    TTA CTC ACA     (SEQ ID NO: 3)
```

TABLE 1B

The sequence of intact HC of Pi

```
       E   V   K   L   L   E   S   G   G   G   L   V   Q   P   G
  1 GAG GTG AAG CTT CTC GAG TCT GGA GGT GGC CTG GTG CAG CCT GGA
    CTC CAC TTC GAA GAG CTC AGA CCT CCA CCG GAC CAC GTC GGA CCT

G   S   L   K   L   S   C   A   A   S   G   F   D   F   S
 46 GGA TCC CTG AAA CTC TCC TGT GCA GCC TCA GGA TTC GAT TTT AGT
    CCT AGG GAC TTT GAG AGG ACA CGT CGG AGT CCT AAG CTA AAA TCA

R   Y   W   M   S   W   V   R   Q   A   P   G   K   G   L
 91 AGA TAC TGG ATG AGT TGG GTC CGG CAG GCT CCA GGG AAA GGG CTA
    TCT ATG ACC TAC TCA ACC CAG GCC GTC CGA GGT CCC TTT CCC GAT

E   W   I   G   E   I   N   P   D   S   S   T   I   N   Y
136 GAA TGG ATT GGA GAA ATT AAT CCA GAT AGC AGT ACG ATA AAC TAT
    CTT ACC TAA CCT CTT TAA TTA GGT CTA TCG TCA TGC TAT TTG ATA

T   P   S   L   K   D   K   F   I   I   S   R   D   N   A
181 ACG CCA TCT CTA AAG GAT AAG TTC ATC ATC TCC AGA GAC AAC GCC
    TGC GGT AGA GAT TTC CTA TTC AAG TAG TAG AGG TCT CTG TTG CGG

K   N   S   L   Y   L   Q   M   S   K   V   R   S   E   D
226 AAA AAT TCG CTG TAC CTG CAA ATG AGC AAA GTG AGA TCT GAG GAC
    TTT TTA AGC GAC ATG GAC GTT TAC TCG TTT CAC TCT AGA CTC CTG

T   A   L   Y   Y   C   A   S   Y   C   G   Y   S   Y   D
271 ACA GCC CTT TAT TAC TGT GCA AGT TAC TGC GGT TAT AGC TAC GAT
    TGT CGG GAA ATA ATG ACA CGT TCA ATG ACG CCA ATA TCG ATG CTA

A   L   D   C   W   G   Q   G   T   S   V   T   V   S   S
316 GCT CTG GAC TGC TGG GGT CAA GGA ACC TCA GTC ACC GTC TCC TCA
    CGA GAC CTG ACG ACC CCA GTT CCT TGG AGT CAG TGG CAG AGG AGT

A   K   T   T   P   P   S   V   Y   P   L   A   P   G   S
361 GCC AAA ACG ACA CCC CCA TCT GTC TAT CCA CTG GCC CCT GGA TCT
    CGG TTT TGC TGT GGG GGT AGA CAG ATA GGT GAC CGG GGA CCT AGA

A   A   Q   T   N   S   M   V   T   L   G   C   L   V   K
406 GCT GCC CAA ACT AAC TCC ATG GTG ACC CTG GGA TGC CTG GTC AAG
    CGA CGG GTT TGA TTG AGG TAC CAC TGG GAC CCT ACG GAC CAG TTC

G   Y   F   P   E   P   V   T   V   T   W   N   S   G   S
451 GGC TAT TTC CCT GAG CCA GTG ACA GTG ACC TGG AAC TCT GGA TCC
    CCG ATA AAG GGA CTC GGT CAC TGT CAC TGG ACC TTG AGA CCT AGG

L   S   S   G   V   H   T   F   P   A   V   L   Q   S   D
496 CTG TCC AGC GGT GTG CAC ACC TTC CCA GCT GTC CTG CAG TCT GAC
    GAC AGG TCG CCA CAC GTG TGG AAG GGT CGA CAG GAC GTC AGA CTG

L   Y   T   L   S   S   S   V   T   V   P   S   S   T   W
541 CTC TAC ACT CTG AGC AGC TCA GTG ACT GTC CCC TCC AGC ACC TGG
    GAG ATG TGA GAC TCG TCG AGT CAC TGA CAG GGG AGG TCG TGG ACC

P   S   E   T   V   T   C   N   V   A   H   P   A   S   S
586 CCC AGC GAG ACC GTC ACC TGC AAC GTT GCC CAC CCG GCC AGC AGC
    GGG TCG CTC TGG CAG TGG ACG TTG CAA CGG GTG GGC CGG TCG TCG
```

TABLE 1B-continued

The sequence of intact HC of Pi

```
          T   K   V   D   K   K   I   V   P   R   D   C   G   C   K
631      ACC AAG GTG GAC AAG AAA ATT GTG CCC AGG GAT TGT GGT TGT AAG
         TGG TTC CAC CTG TTC TTT TAA CAC GGG TCC CTA ACA CCA ACA TTC

P   C   I   C   T   V   P   E   V   S   S   V   F   I   F
676      CCT TGC ATA TGT ACA GTC CCA GAA GTA TCA TCT GTC TTC ATC TTC
         GGA ACG TAT ACA TGT CAG GGT CTT CAT AGT AGA CAG AAG TAG AAG

P   P   K   P   K   D   V   L   T   I   T   L   T   P   K
721      CCC CCA AAG CCC AAG GAT GTG CTC ACC ATT ACT CTG ACT CCT AAG
         GGG GGT TTC GGG TTC CTA CAC GAG TGG TAA TGA GAC TGA GGA TTC

V   T   C   V   V   V   D   I   S   K   D   D   P   E   V
766      GTC ACG TGT GTT GTG GTA GAC ATC AGC AAG GAT GAT CCC GAG GTC
         CAG TGC ACA CAA CAC CAT CTG TAG TCG TTC CTA CTA GGG CTC CAG

Q   F   S   W   F   V   D   D   V   E   V   H   T   A   Q
811      CAG TTC AGC TGG TTT GTA GAT GAT GTG GAG GTG CAC ACA GCT CAG
         GTC AAG TCG ACC AAA CAT CTA CTA CAC CTC CAC GTG TGT CGA GTC

T   Q   P   R   E   E   Q   F   N   S   T   F   R   S   V
856      ACG CAA CCC CGG GAG GAG CAG TTC AAC AGC ACT TTC CGC TCA GTC
         TGC GTT GGG GCC CTC CTC GTC AAG TTG TCG TGA AAG GCG AGT CAG

S   E   L   P   I   M   H   Q   D   W   L   N   G   K   E
901      AGT GAA CTT CCC ATC ATG CAC CAG GAC TGG CTC AAT GGC AAG GAG
         TCA CTT GAA GGG TAG TAC GTG GTC CTG ACC GAG TTA CCG TTC CTC

F   K   C   R   V   N   S   V   A   F   P   A   P   I   E
946      TTC AAA TGC AGG GTC AAC AGT GTA GCT TTC CCT GCC CCC ATC GAG
         AAG TTT ACG TCC CAG TTG TCA CAT CGA AAG GGA CGG GGG TAG CTC

K   T   I   S   K   T   K   G   R   P   K   A   P   Q   V
991      AAA ACC ATC TCC AAA ACC AAA GGC AGA CCG AAG GCT CCA CAG GTG
         TTT TGG TAG AGG TTT TGG TTT CCG TCT GGC TTC CGA GGT GTC CAC

Y   T   I   P   P   P   K   E   Q   M   A   K   D   K   V
1036     TAC ACC ATT CCA CCT CCC AAG GAG CAG ATG GCC AAG GAT AAA GTC
         ATG TGG TAA GGT GGA GGG TTC CTC GTC TAC CGG TTC CTA TTT CAG

S   L   T   C   M   I   T   D   F   F   P   E   D   I   T
1081     AGT CTG ACC TGC ATG ATA ACA GAC TTC TTC CCT GAA GAC ATT ACT
         TCA GAC TGG ACG TAC TAT TGT CTG AAG AAG GGA CTT CTG TAA TGA

V   E   W   Q   W   N   G   Q   P   A   E   N   Y   K   N
1126     GTG GAG TGG CAG TGG AAT GGG CAG CCA GCG GAG AAC TAC AAG AAC
         CAC CTC ACC GTC ACC TTA CCC GTC GGT CGC CTC TTG ATG TTC TTG

T   Q   P   I   M   D   T   D   G   S   Y   F   V   Y   G
1171     ACT CAG CCC ATC ATG GAC ACA GAT GGC TCT TAC TTC GTC TAC GGC
         TGA GTC GGG TAG TAC CTG TGT CTA CCG AGA ATG AAG CAG ATG CCG

K   L   N   V   Q   K   S   N   W   E   A   G   N   T   F
1216     AAG CTC AAT GTG CAG AAG AGC AAC TGG GAG GCA GGA AAT ACT TTC
         TTC GAG TTA CAC GTC TTC TCG TTG ACC CTC CGT CCT TTA TGA AAG

T   C   S   V   L   H   E   G   L   H   N   H   H   T   E
1261     ACC TGC TCT GTG TTA CAT GAG GGC CTG CAC AAC CAC CAT ACT GAG
         TGG ACG AGA CAC AAT GTA CTC CCG GAC GTG TTG GTG GTA TGA CTC

K   S   L   S   H   S   P   G   K       (SEQ ID NO: 4)
1306     AAG AGC CTC TCC CAC TCT CCT GGT AAA       (SEQ ID NO: 5)
         TTC TCG GAG AGG GTG AGA GGA CCA TTT       (SEQ ID NO: 6)
```

TABLE 2A

Deduced amino acid sequence of mouse-human chimeric light chain. Bold-variable region, preceded by a heterologous signal peptide; underlined, human kappa constant region.

| | | | |
|---|---|---|---|
| MYRMQLLSCI | ALSLALVTNS | DIQMTQSPSS | LSASLGGKVS |
| ITCKASQDIN | KYISWYQHKP | GKGPRLLIHY | TSTLQPGIPS |
| RFSGSGSGRD | YSFSISNLEP | EDIATYYCLQ | YDNLYTFGGG |
| TKLEIKRTVA | <u>APSVFIFPPS</u> | <u>DEQLKSGTAS</u> | <u>VVCLLNNFYP</u> |
| <u>REAKVQWKVD</u> | <u>NALQSGNSQE</u> | <u>SVTEQDSKDS</u> | <u>TYSLSSTLTL</u> |
| <u>SKADYEKHKV</u> | <u>YACEVTHQGL</u> | <u>SSPVTKSFNR</u> | <u>GEC</u> |
| (SEQ ID NO: 7) | | | |

TABLE 2B

Deduced amino acid sequence of mouse-human chimeric heavy chain Fab fragment. Bold-variable region, preceded by a heterologous signal peptide; underlined, human CH1 constant domain.

| | | | |
|---|---|---|---|
| MYRMQLLSCI | ALSLALVTNS | EVKLLESGGG | LVQPGGSLKL |
| SCAASGFDFS | RYWMSWVRQA | PGKGLEWIGE | INPDSSTINY |
| TPSLKDKFII | SRDNAKNSLY | LQMSKVRSED | TALYYCASYC |
| GYSYDALDCW | GQGTSVTVSS | ASTKG<u>PSVFP</u> | <u>LAPSSKSTSG</u> |
| <u>GTAALGCLVK</u> | <u>DYFPEPVTVS</u> | <u>WNSGALTSGV</u> | <u>HTFPAVLQSS</u> |
| <u>GLYSLSSVVT</u> | <u>VPSSSLGTQT</u> | <u>YICNVNHKPS</u> | <u>NTKVDKKVEP</u> |
| <u>KSCDKTHTCP</u> | <u>PCP</u> (SEQ ID NO: 8) | | |

FIGS. 6A-6D show Clothia sequence numbering of variable sequences of Pi (FIG. 6A) light chain and (FIG. 6B) heavy chain. The CDR loops and sequences (CDR1, CDR2, and CDR3) are shown in FIG. 6C for the light chain (blue and two shades of green greyscales) CDR1 QDINKY (SEQ ID NO:9); CDR2 YTS (SEQ ID NO:10); CDR3 LQYDNLYT (SEQ ID NO:11). The CDR loops and sequences (CRD1, CDR2, and CDR3) are shown in FIG. 6D for the heavy chain (red, orange and purple greyscales) CDR1 GFDFSRYW (SEQ ID NO:12); CDR2 INPDSSTI (SEQ ID NO:13); CDR3 ASYCGYSYDALDC (SEQ ID NO:14). Produced on IMGT/DomainGapAlign Program version: 4.9.2 (2016-09-26) Ehrenmann F., Kaas Q. and Lefranc M.-P. Nucleic Acids Res., 38, D301-307 (2010). PMID: 19900967. Light chain variable region (SEQ ID NO:15). Heavy chain variable region (SEQ ID NO:16).

REFERENCES

1. Hijazi N, Abu Fanne R, Abramovitch R, et al. Endogenous plasminogen activators mediate progressive intracerebral hemorrhage after traumatic brain injury in mice. Blood. 2015;125:2558-2567 PMID 25673638.
2. Stewart D, Kong M, Novokhatny V, Jesmok G, Marder V J. Distinct dose-dependent effects of plasmin and TPA on coagulation and hemorrhage. Blood. 2003;101:3002-3007 PMID 12446443.
3. collaborators C-t, Shakur H, Roberts I, et al. Effects of tranexamic acid on death, vascular occlusive events, and blood transfusion in trauma patients with significant haemorrhage (CRASH-2): a randomised, placebo-controlled trial. Lancet. 2010;376:23-32 PMID 20554319.
4. Swedberg J E, Harris J M. Natural and engineered plasmin inhibitors: applications and design strategies. Chembiochem. 2012;13:336-348 PMID 22238174.
5. Henry D A, Carless P A, Moxey A J, et al. Anti-fibrinolytic use for minimising perioperative allogeneic blood transfusion. Cochrane Database Syst Rev. 2011:CD001886 PMID 21412876.
6. Mezzano D, Tagle R, Panes O, et al. Hemostatic disorder of uremia: the platelet defect, main determinant of the prolonged bleeding time, is correlated with indices of activation of coagulation and fibrinolysis. Thromb Haemost. 1996;76:312-321 PMID 8883263.
7. Mezzano D, Panes O, Munoz B, et al. Tranexamic acid inhibits fibrinolysis, shortens the bleeding time and improves platelet function in patients with chronic renal failure. Thromb Haemost. 1999;82:1250-1254 PMID 10544908.
8. Rincon F, Rossenwasser R H, Dumont A. The epidemiology of admissions of nontraumatic subarachnoid hemorrhage in the United States. Neurosurgery. 2013;73:217-222; discussion 212-213 PMID 23615089.
9. Rincon F, Mayer S A. The epidemiology of intracerebral hemorrhage in the United States from 1979 to 2008. Neurocrit Care. 2013;19:95-102 PMID 23099848.
10. Oyelese Y, Ananth C V. Postpartum hemorrhage: epidemiology, risk factors, and causes. Clin Obstet Gynecol. 2010;53:147-156 PMID 20142652.
11. Molenaar I Q, Warnaar N, Groen H, Tenvergert E M, Slooff M J, Porte R J. Efficacy and safety of antifibrinolytic drugs in liver transplantation: a systematic review and meta-analysis. Am J Transplant. 2007;7:185-194 PMID 17227567.
12. Tsikouris J P, Suarez J A, Meyerrose GE. Plasminogen activator inhibitor-1: physiologic role, regulation, and the influence of common pharmacologic agents. J Clin Pharmacol. 2002;42:1187-1199 PMID
13. Lee K N, Lee C S, Tae W C, Jackson K W, Christiansen V J, McKee P A. Cross-linking of wild-type and mutant alpha 2-antiplasmins to fibrin by activated factor XIII and by a tissue transglutaminase. J Biol Chem. 2000;275: 37382-37389 PMID
14. Bajzar L. Thrombin activatable fibrinolysis inhibitor and an antifibrinolytic pathway. Arterioscler Thromb Vasc Biol. 2000;20:2511-2518 PMID 11116046.
15. Mutch N J, Thomas L, Moore N R, Lisiak K M, Booth N A. TAFIa, PAI-1 and alpha-antiplasmin: complementary roles in regulating lysis of thrombi and plasma clots. J Thromb Haemost. 2007;5:812-817 PMID 17388801.
16. McEvoy M D, Reeves S T, Reves J G, Spinale F G. Aprotinin in cardiac surgery: a review of conventional and novel mechanisms of action. Anesth Analg. 2007; 105:949-962 PMID 17898372.
17. Beliveau R, Demeule M. Aprotinin and analogs as carriers across the blood-brain barrier. In: Office EP ed. Vol. EP20040700102 European Union; 2005.
18. Turner R B, Liu L, Sazonova I Y, Reed G L. Structural elements that govern the substrate specificity of the clot-dissolving enzyme plasmin. J Biol Chem. 2002;277: 33068-33074 PMID 12080056.
19. Reed G L, 3rd, Matsueda G R, Haber E. Synergistic fibrinolysis: combined effects of plasminogen activators and an antibody that inhibits alpha 2-antiplasmin. Proc Natl Acad Sci USA. 1990;87:1114-1118 PMID 1689060.

20. Wiman B, Caen D. On the kinetics of the reaction between human antiplasmin and plasmin. Eur J Biochem. 1978;84:573-578 PMID 147769.
21. Urano T, de Serrano V S, Gaffney P J, Castellino F J. The activation of human [Glu1]plasminogen by human single-chain urokinase. Arch Biochem Biophys. 1988;264:222-230 PMID
22. Urano T, Sator de Serrano V, Gaffney P J, Castellino F J. Effectors of the activation of human [Glu1]plasminogen by human tissue plasminogen activator. Biochemistry. 1988;27:6522-6528 PMID
23. Albrecht S, Magdolen V, Herzog U, et al. Soluble tissue actor interferes with angiostatin-mediated inhibition of endothelial cell proliferation by lysine-specific interaction with plasminogen kringle domains. Thromb Haemost. 2002;88:1054-1059 PMID 12529759.
24. van Zonneveld A J, Veerman H, Pannekoek H. On the interaction of the finger and the kringle-2 domain of tissue-type plasminogen activator with fibrin. Inhibition of kringle-2 binding to fibrin by epsilon-amino caproic acid. J Biol Chem. 1986;261:14214-14218 PMID 3021732.
25. Hoover-Plow J L, Miles L A, Fless G M, Scanu A M, Plow E F. Comparison of the lysine binding functions of lipoprotein(a) and plasminogen. Biochemistry. 1993;32:13681-13687 PMID 8257702.
26. Manji R A, Grocott H P, Leake J, et al. Seizures following cardiac surgery: the impact of tranexamic acid and other risk factors. Can J Anaesth. 2012;59:6-13 PMID 22065333.
27. Abou-Diwan C, Sniecinski R M, Szlam F, et al. Plasma and cerebral spinal fluid tranexamic acid quantitation in cardiopulmonary bypass patients. J Chromatogr B Analyt Technol Biomed Life Sci. 2011;879:553-556 PMID 21300577.
28. McCormack P L. Tranexamic acid: a review of its use in the treatment of hyperfibrinolysis. Drugs. 2012;72:585-617 PMID 22397329.
29. Berman M, Cardone D, Sharples L, et al. Safety and efficacy of aprotinin and tranexamic acid in pulmonary endarterectomy surgery with hypothermia: review of 200 patients. Ann Thorac Surg. 2010;90:1432-1436 PMID 20971234.
30. Furtmuller R, Schlag M G, Berger M, et al. Tranexamic acid, a widely used antifibrinolytic agent, causes convulsions by a gamma-aminobutyric acid(A) receptor antagonistic effect. J Pharmacol Exp Ther. 2002;301:168-173 PMID 11907171.
31. Ng W, Jerath A, Wasowicz M. Tranexamic acid: a clinical review. Anaesthesiol Intensive Ther. 2015;47:339-350 PMID 25797505.
32. Fergusson D A, Hebert P C, Mazer C D, et al. A comparison of aprotinin and lysine analogues in high-risk cardiac surgery. N Engl J Med. 2008;358:2319-2331 PMID 18480196.
33. Kuitunen A, Hiippala S, Vahtera E, Rasi V, Salmenpera M. The effects of aprotinin and tranexamic acid on thrombin generation and fibrinolytic response after cardiac surgery. Acta Anaesthesiol Scand. 2005;49:1272-1279 PMID 16146463.
34. Henry D A. Fibrinolysis and upper gastrointestinal bleeding. Lancet. 1993;341:527-528 PMID 8094777.
35. Beebe D P, Aronson D L. An automated fibrinolytic assay performed in microtiter plates. Thromb Res. 1987;47:123-128 PMID 3116709.
36. Thomas S G, Calaminus S D, Auger J M, Watson S P, Machesky L M. Studies on the actin-binding protein HS1 in platelets. BMC Cell Biol. 2007;8:46 PMID 17996076.
37. Liu Y, Jennings N L, Dart A M, Du X J. Standardizing a simpler, more sensitive and accurate tail bleeding assay in mice. World J Exp Med. 2012;2:30-36 PMID 24520531.

The invention claimed is:

1. A method of inhibiting plasmin activity in a subject in need thereof comprising administering to the subject an effective amount of a plasmin inhibiting composition comprising a plasmin protease domain-specific binding monoclonal antibody or functional fragment thereof that inhibits fibrinolysis, wherein the monoclonal antibody or functional fragment thereof comprises variable region light chain CDR amino acid sequences CDR1, CDR2 and CDR3 defined by SEQ ID NOS:9-11 and variable region heavy chain CDR amino acid sequences CDR1, CDR2 and CDR3 defined by SEQ ID NOS:12-14.

2. The method of claim 1, wherein the monoclonal antibody or functional fragment thereof inhibits plasmin cleavage of Factor V protein.

3. The method of claim 1, wherein the monoclonal antibody or functional fragment thereof inhibits plasmin cleavage of tripeptide paranitroanilide substrate more potently than epsilon amino caproic acid.

4. The method of claim 1, wherein the subject is a human.

5. The method of claim 1, wherein the monoclonal antibody or functional fragment thereof is a non-competitive inhibitor of plasmin activity.

6. The method of claim 1, wherein the monoclonal antibody or functional fragment thereof requires loops four and five of plasmin to mediate binding of the monoclonal antibody to plasmin.

7. The method of claim 1, wherein the monoclonal antibody or functional fragment thereof does not specifically bind non-plasmin serine-proteases trypsin, thrombin, activated protein C, kallikrein, neutrophil elastase, or a combination thereof.

8. The method of claim 1, wherein the monoclonal antibody of functional fragment thereof comprises a variable region light chain amino acid sequence at least 90% identical to SEQ ID NO:15 and a variable region heavy chain amino acid sequence at least 90% identical to SEQ ID NO:16.

9. A method of treating hemorrhage in a subject in need thereof comprising administering to the patient an effective amount of a pharmaceutical composition comprising a plasmin protease domain-specific binding monoclonal antibody or functional fragment thereof and a pharmaceutically acceptable excipient wherein the monoclonal antibody or functional fragment thereof comprises variable region light chain CDR amino acid sequences CDR1, CDR2 and CDR3 defined by SEQ ID NOS:9-11 and variable region heavy chain CDR amino acid sequences CDR1, CDR2 and CDR3 defined by SEQ ID NOS:12-14.

10. The method of claim 9, wherein the monoclonal antibody or functional fragment thereof inhibits fibrinolysis.

11. The method of claim 9, wherein the monoclonal antibody or functional fragment thereof inhibits plasmin cleavage of Factor V protein.

12. The method of claim 9, wherein the monoclonal antibody or functional fragment thereof inhibits plasmin cleavage of tripeptide paranitroanilide substrate more potently than epsilon amino caproic acid.

13. The method of claim 9, wherein the subject is a human.

14. The method of claim 9, wherein the monoclonal antibody or functional fragment thereof is a non-competitive inhibitor of plasmin activity.

15. The method of claim 9, wherein the monoclonal antibody or functional fragment thereof specifically binds loop sequences 4 and 5 in plasmin protease domain.

16. The method of claim 9, wherein the monoclonal antibody or functional fragment thereof does not specifically bind non-plasmin serine-proteases trypsin, thrombin, activated protein C, kallikrein, neutrophil elastase, or a combination thereof.

17. The method of claim 9, wherein the monoclonal antibody of functional fragment thereof comprises a variable region light chain amino acid sequence at least 90% identical to SEQ ID NO:15 and a variable region heavy chain amino acid sequence at least 90% identical to SEQ ID NO:16.

18. A pharmaceutical composition for treating hemorrhage comprising a therapeutically effective amount of an antifibrinolytic composition comprising a plasmin-specific monoclonal antibody or functional fragment thereof and a pharmaceutically acceptable carrier, wherein the monoclonal antibody or functional fragment thereof comprises variable region light chain CDR amino acid sequences CDR1, CDR2 and CDR3 defined by SEQ ID NOS:9-11 and variable region heavy chain CDR amino acid sequences CDR1, CDR2 and CDR3 defined by SEQ ID NOS:12-14.

19. The pharmaceutical composition of claim 18, wherein the monoclonal antibody of functional fragment thereof comprises a variable region light chain amino acid sequence at least 90% identical to SEQ ID NO:15 and a variable region heavy chain amino acid sequence at least 90% identical to SEQ ID NO:16.

* * * * *

SEQUENCE LISTING

```
<160> NUMBER OF SEQ ID NOS: 16

<210> SEQ ID NO 1
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Asp Ile Gln Met Thr Gln Ser Pro Ser Ser Leu Ser Ala Ser Leu Gly
1               5                   10                  15

Gly Lys Val Ser Ile Thr Cys Lys Ala Ser Gln Asp Ile Asn Lys Tyr
            20                  25                  30

Ile Ser Trp Tyr Gln His Lys Pro Gly Lys Gly Pro Arg Leu Leu Ile
        35                  40                  45

His Tyr Thr Ser Thr Leu Gln Pro Gly Ile Pro Ser Arg Phe Ser Gly
    50                  55                  60

Ser Gly Ser Gly Arg Asp Tyr Ser Phe Ser Ile Ser Asn Leu Glu Pro
65                  70                  75                  80

Glu Asp Ile Ala Thr Tyr Tyr Cys Leu Gln Tyr Asp Asn Leu Tyr Thr
                85                  90                  95

Phe Gly Gly Gly Thr Lys Leu Glu Ile Lys Arg Ala Asp Ala Ala Pro
            100                 105                 110
```

```
Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
    130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
                180                 185                 190

Cys Glu Ala Thr His Lys Thr Ser Thr Ser Pro Ile Val Lys Ser Phe
        195                 200                 205

Asn Trp Asn Glu Cys
    210
```

<210> SEQ ID NO 2
<211> LENGTH: 639
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(639)

<400> SEQUENCE: 2

```
gac atc cag atg aca cag tct cca tcc tca ctg tct gca tct ctg ggg     48
Asp Ile Gln Met Thr Gln Ser Pro Ser Ser Leu Ser Ala Ser Leu Gly
1               5                   10                  15 ggc aaa gtc tcc atc act tgc aag gca agc caa gac att aac aag tat     96
Gly Lys Val Ser Ile Thr Cys Lys Ala Ser Gln Asp Ile Asn Lys Tyr
            20                  25                  30 att tct tgg tac caa cac aag cct gga aaa ggt cct agg ctg ctc ata    144
Ile Ser Trp Tyr Gln His Lys Pro Gly Lys Gly Pro Arg Leu Leu Ile
        35                  40                  45 cat tac aca tct aca tta cag cca ggc atc cca tca agg ttc agt gga    192
His Tyr Thr Ser Thr Leu Gln Pro Gly Ile Pro Ser Arg Phe Ser Gly
    50                  55                  60 agt ggg tct ggg aga gat tat tcc ttc agc atc agc aac ctg gag cct    240
Ser Gly Ser Gly Arg Asp Tyr Ser Phe Ser Ile Ser Asn Leu Glu Pro
65                  70                  75                  80 gaa gat att gca act tat tat tgt cta cag tat gat aat ctg tac acg    288
Glu Asp Ile Ala Thr Tyr Tyr Cys Leu Gln Tyr Asp Asn Leu Tyr Thr
                85                  90                  95 ttc gga ggg ggg acc aag ctg gaa ata aaa cgg gca gat gct gca cca    336
Phe Gly Gly Gly Thr Lys Leu Glu Ile Lys Arg Ala Asp Ala Ala Pro
            100                 105                 110 act gta tcc atc ttc cca cca tcc agt gag cag tta aca tct gga ggt    384
Thr Val Ser Ile Phe Pro Pro Ser Ser Glu Gln Leu Thr Ser Gly Gly
        115                 120                 125 gcc tca gtc gtg tgc ttc ttg aac aac ttc tac ccc aaa gac atc aat    432
Ala Ser Val Val Cys Phe Leu Asn Asn Phe Tyr Pro Lys Asp Ile Asn
    130                 135                 140 gtc aag tgg aag att gat ggc agt gaa cga caa aat ggc gtc ctg aac    480
Val Lys Trp Lys Ile Asp Gly Ser Glu Arg Gln Asn Gly Val Leu Asn
145                 150                 155                 160 agt tgg act gat cag gac agc aaa gac agc acc tac agc atg agc agc    528
Ser Trp Thr Asp Gln Asp Ser Lys Asp Ser Thr Tyr Ser Met Ser Ser
                165                 170                 175
```

| | | | | | | | | | | | | | | | |
|---|---|---|---|---|---|---|---|---|---|---|---|---|---|---|---|
| acc | ctc | acg | ttg | acc | aag | gac | gaa | tat | gaa | cga | cat | aac | agc | tat | acc | 576
| Thr | Leu | Thr | Leu | Thr | Lys | Asp | Glu | Tyr | Glu | Arg | His | Asn | Ser | Tyr | Thr |
|  |  |  | 180 |  |  |  |  | 185 |  |  |  |  | 190 |  |  |

| | | | | | | | | | | | | | | | |
|---|---|---|---|---|---|---|---|---|---|---|---|---|---|---|---|
| tgt | gag | gcc | act | cac | aag | aca | tca | act | tca | ccc | att | gtc | aag | agc | ttc | 624
| Cys | Glu | Ala | Thr | His | Lys | Thr | Ser | Thr | Ser | Pro | Ile | Val | Lys | Ser | Phe |
|  |  | 195 |  |  |  |  | 200 |  |  |  |  | 205 |  |  |  | aac tgg aat gag tgt                                                     639
Asn Trp Asn Glu Cys
    210

<210> SEQ ID NO 3
<211> LENGTH: 639
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
acactcattc cagttgaagc tcttgacaat gggtgaagtt gatgtcttgt gagtggcctc      60
acaggtatag ctgttatgtc gttcatattc gtccttggtc aacgtgaggg tgctgctcat     120
gctgtaggtg ctgtctttgc tgtcctgatc agtccaactg ttcaggacgc cattttgtcg     180
ttcactgcca tcaatcttcc acttgacatt gatgtctttg gggtagaagt tgttcaagaa     240
gcacacgact gaggcacctc cagatgttaa ctgctcactg gatggtggga agatggatac     300
agttggtgca gcatctgccc gttttatttc cagcttggtc cccctccga acgtgtacag      360 attatcatac tgtagacaat aataagttgc aatatcttca ggctccaggt tgctgatgct     420
gaaggaataa tctctcccag acccacttcc actgaacctt gatgggatgc ctggctgtaa     480
tgtagatgtg taatgtatga gcagcctagg acctttccca ggcttgtgtt ggtaccaaga     540
aatatacttg ttaatgtctt ggcttgcctt gcaagtgatg gagactttgc cccccagaga     600
tgcagacagt gaggatggag actgtgtcat ctggatgtc                            639

<210> SEQ ID NO 4
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Thr Ile Asn Tyr Thr Pro Ser Leu
    50                  55                  60

Lys Asp Lys Phe Ile Ile Ser Arg Asp Asn Ala Lys Asn Ser Leu Tyr
65                  70                  75                  80

Leu Gln Met Ser Lys Val Arg Ser Glu Asp Thr Ala Leu Tyr Tyr Cys
                85                  90                  95

Ala Ser Tyr Cys Gly Tyr Ser Tyr Asp Ala Leu Asp Cys Trp Gly Gln
            100                 105                 110

Gly Thr Ser Val Thr Val Ser Ser Ala Lys Thr Thr Pro Pro Ser Val

```
            115                 120                 125
Tyr Pro Leu Ala Pro Gly Ser Ala Ala Gln Thr Asn Ser Met Val Thr
    130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Val Thr Val Pro Ser
            180                 185                 190

Ser Thr Trp Pro Ser Glu Thr Val Thr Cys Asn Val Ala His Pro Ala
                195                 200                 205

Ser Ser Thr Lys Val Asp Lys Lys Ile Val Pro Arg Asp Cys Gly Cys
    210                 215                 220

Lys Pro Cys Ile Cys Thr Val Pro Glu Val Ser Ser Val Phe Ile Phe
225                 230                 235                 240

Pro Pro Lys Pro Lys Asp Val Leu Thr Ile Thr Leu Thr Pro Lys Val
                245                 250                 255

Thr Cys Val Val Val Asp Ile Ser Lys Asp Asp Pro Glu Val Gln Phe
            260                 265                 270

Ser Trp Phe Val Asp Asp Val Glu Val His Thr Ala Gln Thr Gln Pro
    275                 280                 285

Arg Glu Glu Gln Phe Asn Ser Thr Phe Arg Ser Val Ser Glu Leu Pro
290                 295                 300

Ile Met His Gln Asp Trp Leu Asn Gly Lys Glu Phe Lys Cys Arg Val
305                 310                 315                 320

Asn Ser Val Ala Phe Pro Ala Pro Ile Glu Lys Thr Ile Ser Lys Thr
                325                 330                 335

Lys Gly Arg Pro Lys Ala Pro Gln Val Tyr Thr Ile Pro Pro Pro Lys
            340                 345                 350

Glu Gln Met Ala Lys Asp Lys Val Ser Leu Thr Cys Met Ile Thr Asp
    355                 360                 365

Phe Phe Pro Glu Asp Ile Thr Val Glu Trp Gln Trp Asn Gly Gln Pro
370                 375                 380

Ala Glu Asn Tyr Lys Asn Thr Gln Pro Ile Met Asp Thr Asp Gly Ser
385                 390                 395                 400

Tyr Phe Val Tyr Gly Lys Leu Asn Val Gln Lys Ser Asn Trp Glu Ala
                405                 410                 415

Gly Asn Thr Phe Thr Cys Ser Val Leu His Glu Gly Leu His Asn His
            420                 425                 430

His Thr Glu Lys Ser Leu Ser His Ser Pro Gly Lys
    435                 440

<210> SEQ ID NO 5
<211> LENGTH: 1332
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1332)

<400> SEQUENCE: 5 gag gtg aag ctt ctc gag tct gga ggt ggc ctg gtg cag cct gga gga   48
Glu Val Lys Leu Leu Glu Ser Gly Gly Gly Leu Val Gln Pro Gly Gly
1               5                   10                  15
```

|                                                                                         |      |
|-----------------------------------------------------------------------------------------|------|
| tcc ctg aaa ctc tcc tgt gca gcc tca gga ttc gat ttt agt aga tac                         | 96   |
| Ser Leu Lys Leu Ser Cys Ala Ala Ser Gly Phe Asp Phe Ser Arg Tyr                         |      |
|         20                  25                  30                                      |      |
| tgg atg agt tgg gtc cgg cag gct cca ggg aaa ggg cta gaa tgg att                         | 144  |
| Trp Met Ser Trp Val Arg Gln Ala Pro Gly Lys Gly Leu Glu Trp Ile                         |      |
|     35                  40                  45                                          |      |
| gga gaa att aat cca gat agc agt acg ata aac tat acg cca tct cta                         | 192  |
| Gly Glu Ile Asn Pro Asp Ser Ser Thr Ile Asn Tyr Thr Pro Ser Leu                         |      |
| 50                  55                  60                                              |      |
| aag gat aag ttc atc atc tcc aga gac aac gcc aaa aat tcg ctg tac                         | 240  |
| Lys Asp Lys Phe Ile Ile Ser Arg Asp Asn Ala Lys Asn Ser Leu Tyr                         |      |
| 65                  70                  75                  80                          |      |
| ctg caa atg agc aaa gtg aga tct gag gac aca gcc ctt tat tac tgt                         | 288  |
| Leu Gln Met Ser Lys Val Arg Ser Glu Asp Thr Ala Leu Tyr Tyr Cys                         |      |
|             85                  90                  95                                  |      |
| gca agt tac tgc ggt tat agc tac gat gct ctg gac tgc tgg ggt caa                         | 336  |
| Ala Ser Tyr Cys Gly Tyr Ser Tyr Asp Ala Leu Asp Cys Trp Gly Gln                         |      |
|                 100                 105                 110                             |      |
| gga acc tca gtc acc gtc tcc tca gcc aaa acg aca ccc cca tct gtc                         | 384  |
| Gly Thr Ser Val Thr Val Ser Ser Ala Lys Thr Thr Pro Pro Ser Val                         |      |
|             115                 120                 125                                 |      |
| tat cca ctg gcc cct gga tct gct gcc caa act aac tcc atg gtg acc                         | 432  |
| Tyr Pro Leu Ala Pro Gly Ser Ala Ala Gln Thr Asn Ser Met Val Thr                         |      |
| 130                 135                 140                                             |      |
| ctg gga tgc ctg gtc aag ggc tat ttc cct gag cca gtg aca gtg acc                         | 480  |
| Leu Gly Cys Leu Val Lys Gly Tyr Phe Pro Glu Pro Val Thr Val Thr                         |      |
| 145                 150                 155                 160                         |      |
| tgg aac tct gga tcc ctg tcc agc ggt gtg cac acc ttc cca gct gtc                         | 528  |
| Trp Asn Ser Gly Ser Leu Ser Ser Gly Val His Thr Phe Pro Ala Val                         |      |
|                 165                 170                 175                             |      |
| ctg cag tct gac ctc tac act ctg agc agc tca gtg act gtc ccc tcc                         | 576  |
| Leu Gln Ser Asp Leu Tyr Thr Leu Ser Ser Ser Val Thr Val Pro Ser                         |      |
|             180                 185                 190                                 |      |
| agc acc tgg ccc agc gag acc gtc acc tgc aac gtt gcc cac ccg gcc                         | 624  |
| Ser Thr Trp Pro Ser Glu Thr Val Thr Cys Asn Val Ala His Pro Ala                         |      |
|             195                 200                 205                                 |      |
| agc agc acc aag gtg gac aag aaa att gtg ccc agg gat tgt ggt tgt                         | 672  |
| Ser Ser Thr Lys Val Asp Lys Lys Ile Val Pro Arg Asp Cys Gly Cys                         |      |
| 210                 215                 220                                             |      |
| aag cct tgc ata tgt aca gtc cca gaa gta tca tct gtc ttc atc ttc                         | 720  |
| Lys Pro Cys Ile Cys Thr Val Pro Glu Val Ser Ser Val Phe Ile Phe                         |      |
| 225                 230                 235                 240                         |      |
| ccc cca aag ccc aag gat gtg ctc acc att act ctg act cct aag gtc                         | 768  |
| Pro Pro Lys Pro Lys Asp Val Leu Thr Ile Thr Leu Thr Pro Lys Val                         |      |
|                 245                 250                 255                             |      |
| acg tgt gtt gtg gta gac atc agc aag gat gat ccc gag gtc cag ttc                         | 816  |
| Thr Cys Val Val Val Asp Ile Ser Lys Asp Asp Pro Glu Val Gln Phe                         |      |
|             260                 265                 270                                 |      |
| agc tgg ttt gta gat gat gtg gag gtg cac aca gct cag acg caa ccc                         | 864  |
| Ser Trp Phe Val Asp Asp Val Glu Val His Thr Ala Gln Thr Gln Pro                         |      |
|         275                 280                 285                                     |      |
| cgg gag gag cag ttc aac agc act ttc cgc tca gtc agt gaa ctt ccc                         | 912  |
| Arg Glu Glu Gln Phe Asn Ser Thr Phe Arg Ser Val Ser Glu Leu Pro                         |      |
|     290                 295                 300                                         |      |
| atc atg cac cag gac tgg ctc aat ggc aag gag ttc aaa tgc agg gtc                         | 960  |
| Ile Met His Gln Asp Trp Leu Asn Gly Lys Glu Phe Lys Cys Arg Val                         |      |
| 305                 310                 315                 320                         |      |
| aac agt gta gct ttc cct gcc ccc atc gag aaa acc atc tcc aaa acc                         | 1008 |
| Asn Ser Val Ala Phe Pro Ala Pro Ile Glu Lys Thr Ile Ser Lys Thr                         |      |

|  |  |  |  |  |  |  |  |  |  |  |  |  |  |  |  |  |
|---|---|---|---|---|---|---|---|---|---|---|---|---|---|---|---|---|
|  |  |  | 325 |  |  |  | 330 |  |  |  | 335 |  |  |  |  |  |
| aaa | ggc | aga | ccg | aag | gct | cca | cag | gtg | tac | acc | att | cca | cct | ccc | aag | 1056 |
| Lys | Gly | Arg | Pro | Lys | Ala | Pro | Gln | Val | Tyr | Thr | Ile | Pro | Pro | Pro | Lys |  |
|  |  | 340 |  |  |  |  | 345 |  |  |  |  | 350 |  |  |  |  |
| gag | cag | atg | gcc | aag | gat | aaa | gtc | agt | ctg | acc | tgc | atg | ata | aca | gac | 1104 |
| Glu | Gln | Met | Ala | Lys | Asp | Lys | Val | Ser | Leu | Thr | Cys | Met | Ile | Thr | Asp |  |
|  | 355 |  |  |  |  | 360 |  |  |  |  | 365 |  |  |  |  |  |
| ttc | ttc | cct | gaa | gac | att | act | gtg | gag | tgg | cag | tgg | aat | ggg | cag | cca | 1152 |
| Phe | Phe | Pro | Glu | Asp | Ile | Thr | Val | Glu | Trp | Gln | Trp | Asn | Gly | Gln | Pro |  |
| 370 |  |  |  |  | 375 |  |  |  |  | 380 |  |  |  |  |  |  |
| gcg | gag | aac | tac | aag | aac | act | cag | ccc | atc | atg | gac | aca | gat | ggc | tct | 1200 |
| Ala | Glu | Asn | Tyr | Lys | Asn | Thr | Gln | Pro | Ile | Met | Asp | Thr | Asp | Gly | Ser |  |
| 385 |  |  |  | 390 |  |  |  |  | 395 |  |  |  |  | 400 |  |  |
| tac | ttc | gtc | tac | ggc | aag | ctc | aat | gtg | cag | aag | agc | aac | tgg | gag | gca | 1248 |
| Tyr | Phe | Val | Tyr | Gly | Lys | Leu | Asn | Val | Gln | Lys | Ser | Asn | Trp | Glu | Ala |  |
|  |  |  |  | 405 |  |  |  |  | 410 |  |  |  |  | 415 |  |  |
| gga | aat | act | ttc | acc | tgc | tct | gtg | tta | cat | gag | ggc | ctg | cac | aac | cac | 1296 |
| Gly | Asn | Thr | Phe | Thr | Cys | Ser | Val | Leu | His | Glu | Gly | Leu | His | Asn | His |  |
|  |  |  | 420 |  |  |  |  | 425 |  |  |  |  | 430 |  |  |  |
| cat | act | gag | aag | agc | ctc | tcc | cac | tct | cct | ggt | aaa |  |  |  |  | 1332 |
| His | Thr | Glu | Lys | Ser | Leu | Ser | His | Ser | Pro | Gly | Lys |  |  |  |  |  |
|  |  | 435 |  |  |  |  | 440 |  |  |  |  |  |  |  |  |  |

<210> SEQ ID NO 6
<211> LENGTH: 1332
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 6

```
tttaccagga gagtgggaga ggctcttctc agtatggtgg ttgtgcaggc cctcatgtaa     60
cacagagcag gtgaaagtat ttcctgcctc ccagttgctc ttctgcacat tgagcttgcc    120
gtagacgaag taagagccat ctgtgtccat gatgggctga gtgttcttgt agttctccgc    180
tggctgccca ttccactgcc actccacagt aatgtcttca gggaagaagt ctgttatcat    240
gcaggtcaga ctgactttat ccttggccat ctgctccttg gaggtggaa tggtgtacac    300
ctgtggagcc tcggtctgc ctttggtttt ggagatggtt ttctcgatgg gggcagggaa    360
agctacactg ttgaccctgc atttgaactc cttgccattg agccagtcct ggtgcatgat    420
gggaagttca ctgactgagc ggaaagtgct gttgaactgc cctcccggg gttgcgtctg    480
agctgtgtgc acctccacat catctacaaa ccagctgaac tggacctcgg gatcatcctt    540
gctgatgtct accacaacac acgtgacctt aggagtcaga gtaatggtga gcacatcctt    600
gggctttggg gggaagatga agacagatga tacttctggg actgtacata tgcaaggctt    660
acaaccacaa tccctgggca aattttcttt gtccaccttg gtgctgctgg ccgggtgggc    720
aacgttgcag gtgacggtct cgctgggcca ggtgctggag ggacagtca ctgagctgct    780
cagagtgtag aggtcagact gcaggacagc tgggaaggtg tgcacaccgc tggacaggga    840
tccagagttc caggtcactg tcactggctc agggaaatag cccttgacca ggcatcccag    900
ggtcaccatg gagttagttt gggcagcaga tccaggggcc agtggataga cagatggggg    960
tgtcgtttg gctgaggaga cggtgactga ggttccttga ccccagcagt ccagagcatc   1020
gtagctataa ccgcagtaac ttgcacagta ataaagggct gtgtcctcag atctcacttt   1080
gctcatttgc aggtacagcg aattttggc gttgtctctg gagatgatga acttatcctt   1140
```

```
tagagatggc gtatagttta tcgtactgct atctggatta atttctccaa tccattctag    1200
ccctttccct ggagcctgcc ggacccaact catccagtat ctactaaaat cgaatcctga    1260
ggctgcacag gagagtttca gggatcctcc aggctgcacc aggccacctc cagactcgag    1320
aagcttcacc tc                                                        1332
```

<210> SEQ ID NO 7
<211> LENGTH: 233
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Tyr Arg Met Gln Leu Leu Ser Cys Ile Ala Leu Ser Leu Ala Leu
1               5                   10                  15

Val Thr Asn Ser Asp Ile Gln Met Thr Gln Ser Pro Ser Ser Leu Ser
                20                  25                  30

Ala Ser Leu Gly Gly Lys Val Ser Ile Thr Cys Lys Ala Ser Gln Asp
            35                  40                  45

Ile Asn Lys Tyr Ile Ser Trp Tyr Gln His Lys Pro Gly Lys Gly Pro
        50                  55                  60

Arg Leu Leu Ile His Tyr Thr Ser Thr Leu Gln Pro Gly Ile Pro Ser
65                  70                  75                  80

Arg Phe Ser Gly Ser Gly Ser Gly Arg Asp Tyr Ser Phe Ser Ile Ser
                85                  90                  95

Asn Leu Glu Pro Glu Asp Ile Ala Thr Tyr Tyr Cys Leu Gln Tyr Asp
            100                 105                 110

Asn Leu Tyr Thr Phe Gly Gly Gly Thr Lys Leu Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 8
<211> LENGTH: 253
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Tyr Arg Met Gln Leu Leu Ser Cys Ile Ala Leu Ser Leu Ala Leu
1               5                   10                  15

Val Thr Asn Ser Glu Val Lys Leu Leu Glu Ser Gly Gly Gly Leu Val

```
                20                  25                  30
Gln Pro Gly Gly Ser Leu Lys Leu Ser Cys Ala Ala Ser Gly Phe Asp
            35                  40                  45

Phe Ser Arg Tyr Trp Met Ser Trp Val Arg Gln Ala Pro Gly Lys Gly
        50                  55                  60

Leu Glu Trp Ile Gly Glu Ile Asn Pro Asp Ser Ser Thr Ile Asn Tyr
 65                 70                  75                  80

Thr Pro Ser Leu Lys Asp Lys Phe Ile Ile Ser Arg Asp Asn Ala Lys
                85                  90                  95

Asn Ser Leu Tyr Leu Gln Met Ser Lys Val Arg Ser Glu Asp Thr Ala
            100                 105                 110

Leu Tyr Tyr Cys Ala Ser Tyr Cys Gly Tyr Ser Tyr Asp Ala Leu Asp
        115                 120                 125

Cys Trp Gly Gln Gly Thr Ser Val Thr Val Ser Ala Ser Thr Lys
130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Val Glu Pro
225                 230                 235                 240

Lys Ser Cys Asp Lys Thr His Thr Cys Pro Pro Cys Pro
                245                 250

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gln Asp Ile Asn Lys Tyr
1               5

<210> SEQ ID NO 10
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Tyr Thr Ser
1

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 11

Leu Gln Tyr Asp Asn Leu Tyr Thr
1               5

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Phe Asp Phe Ser Arg Tyr Trp
1               5

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ile Asn Pro Asp Ser Ser Thr Ile
1               5

<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ala Ser Tyr Cys Gly Tyr Ser Tyr Asp Ala Leu Asp Cys
1               5                   10

<210> SEQ ID NO 15
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Asp Ile Gln Met Thr Gln Ser Pro Ser Ser Leu Ser Ala Ser Leu Gly
1               5                   10                  15

Gly Lys Val Ser Ile Thr Cys Lys Ala Ser Gln Asp Ile Asn Lys Tyr
            20                  25                  30

Ile Ser Trp Tyr Gln His Lys Pro Gly Lys Pro Arg Leu Leu Ile
        35                  40                  45

His Tyr Thr Ser Thr Leu Gln Pro Gly Ile Pro Ser Arg Phe Ser Gly
    50                  55                  60

Ser Gly Ser Gly Arg Asp Tyr Ser Phe Ser Ile Ser Asn Leu Glu Pro
65                  70                  75                  80

Glu Asp Ile Ala Thr Tyr Tyr Cys Leu Gln Tyr Asp Asn Leu Tyr Thr
                85                  90                  95

Phe Gly Gly Gly Thr Lys Leu Glu Ile Lys

-continued

```
<210> SEQ ID NO 16
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Ser Thr Ile Asn Tyr Thr Pro Ser Leu
    50                  55                  60

Lys Asp Lys Phe Ile Ile Ser Arg Asp Asn Ala Lys Asn Ser Leu Tyr
65                  70                  75                  80

Leu Gln Met Ser Lys Val Arg Ser Glu Asp Thr Ala Leu Tyr Tyr Cys
            85                  90                  95

Ala Ser Tyr Cys Gly Tyr Ser Tyr Asp Ala Leu Asp Cys Trp Gly Gln
            100                 105                 110

Gly Thr Ser Val Thr Val Ser Ser
            115                 120
```